United States Patent
Kadaba et al.

(10) Patent No.: US 11,737,892 B1
(45) Date of Patent: Aug. 29, 2023

(54) INTERVERTEBRAL SPACER WITH RAMPED INTEGRAL EXPANSION MECHANISM AND STEPPED LOCKING MECHANISM

(71) Applicant: IngeniumSpine, LLC, Phoenix, AZ (US)

(72) Inventors: Murali Kadaba, Austin, TX (US); Damien Shulock, San Francisco, CA (US); Dennis Crandall, Mesa, AZ (US)

(73) Assignee: Ingeniumspine, LLC, Phoenix, AZ (US)

( * ) Notice: Subject to any disclaimer, the term of this patent is extended or adjusted under 35 U.S.C. 154(b) by 0 days.

(21) Appl. No.: 18/098,567

(22) Filed: Jan. 18, 2023

(51) Int. Cl.
*A61F 2/44* (2006.01)
*A61F 2/46* (2006.01)
*A61F 2/30* (2006.01)

(52) U.S. Cl.
CPC .......... *A61F 2/447* (2013.01); *A61F 2/30771* (2013.01); *A61F 2/4611* (2013.01); *A61F 2002/30176* (2013.01); *A61F 2002/30471* (2013.01); *A61F 2002/30476* (2013.01); *A61F 2002/30518* (2013.01); *A61F 2002/30904* (2013.01); *A61F 2002/30937* (2013.01); *A61F 2002/4615* (2013.01)

(58) Field of Classification Search
CPC .. A61F 2/44; A61F 2/442; A61F 2/447; A61F 2/30771; A61F 2/4611; A61F 2002/30176; A61F 2002/30471; A61F 2002/30476; A61F 2002/30518; A61F 2002/30904; A61F 2002/30937; A61F 2002/4615

USPC .............................. 623/17.11–17.16; 606/99
See application file for complete search history.

(56) References Cited

U.S. PATENT DOCUMENTS

| | | | |
|---|---|---|---|
| 6,193,757 B1 * | 2/2001 | Foley .................... | A61F 2/4455 623/17.16 |
| 6,491,724 B1 * | 12/2002 | Ferree .................... | A61F 2/447 623/17.11 |
| 7,044,971 B2 * | 5/2006 | Suddaby ............... | A61F 2/4455 623/17.11 |
| 9,399,130 B2 | 7/2016 | Suddaby | |
| 2010/0137987 A1 * | 6/2010 | Diao .................. | A61B 17/7095 623/17.11 |
| 2010/0191336 A1 * | 7/2010 | Greenhalgh .......... | A61F 2/4455 623/17.16 |
| 2013/0041471 A1 * | 2/2013 | Siegal ................ | A61B 17/3472 623/17.16 |

(Continued)

*Primary Examiner* — Jessica Weiss
(74) *Attorney, Agent, or Firm* — Etherton Law Group, LLC

(57) ABSTRACT

An expandable intervertebral spacer system having a top plate and a bottom plate forming a cage. The top, bottom, and sides of the cage have openings to receive bone graft material. At least one ramp extends into the cage from the top plate or bottom plate. The top plate and bottom plate are connected together at the proximal end of the cage at a hinge. The cage is expanded by inserting a pushrod into the proximal end of the cage against the ramp and forcing the top and bottom plates apart at a desired angle. A locking mechanism at the distal end of the cage locks the plates apart using a ratchet-like mechanism in which a torsion spring biases a movable post against a stationary post, such that the saw teeth of the movable post and stationary post cooperate to lock the top and bottom plates apart.

21 Claims, 23 Drawing Sheets

(56) References Cited

U.S. PATENT DOCUMENTS

2014/0343678 A1\* 11/2014 Suddaby ............... A61F 2/4611
                                                      623/17.16
2019/0083279 A1\* 3/2019 Suddaby ................. A61F 2/447

\* cited by examiner

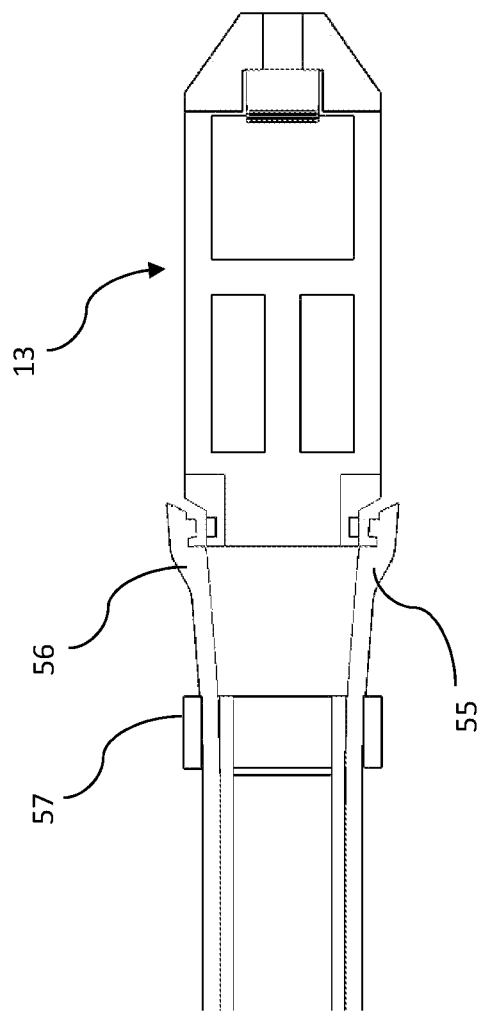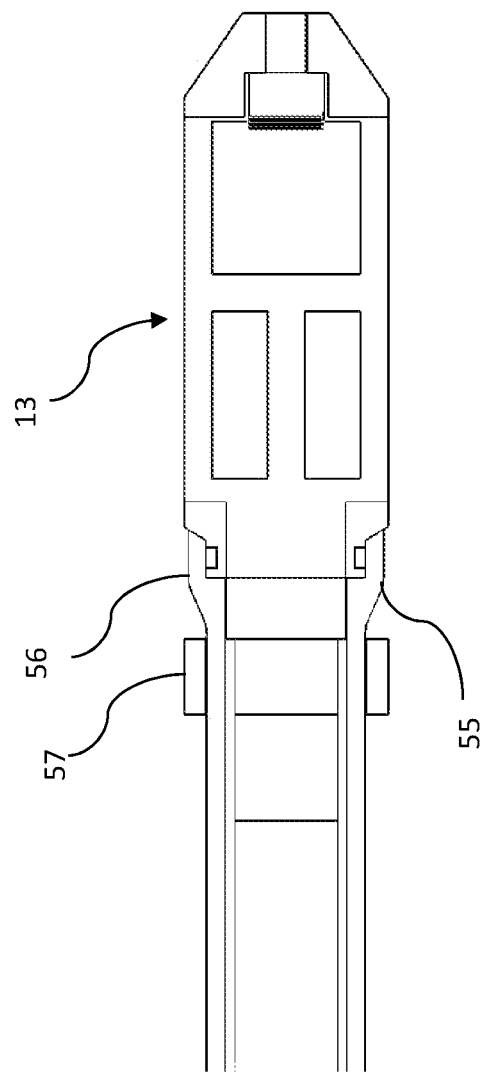

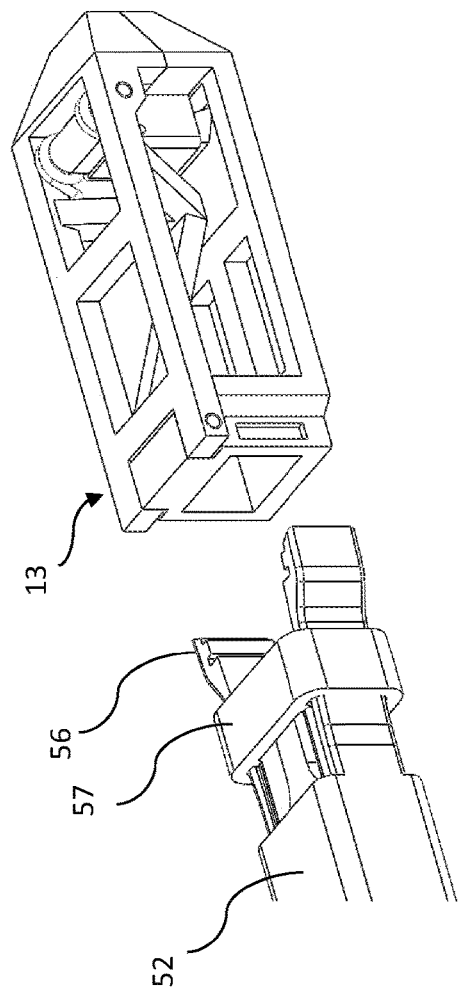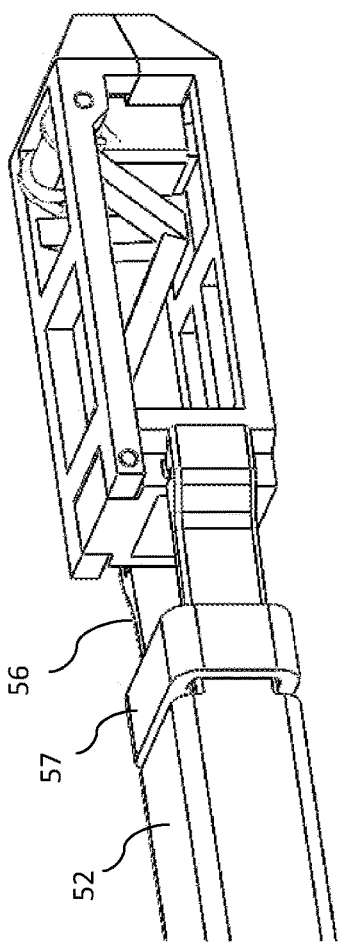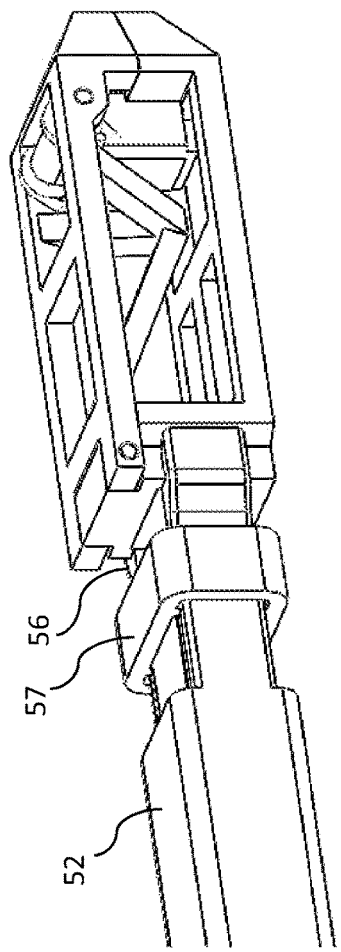

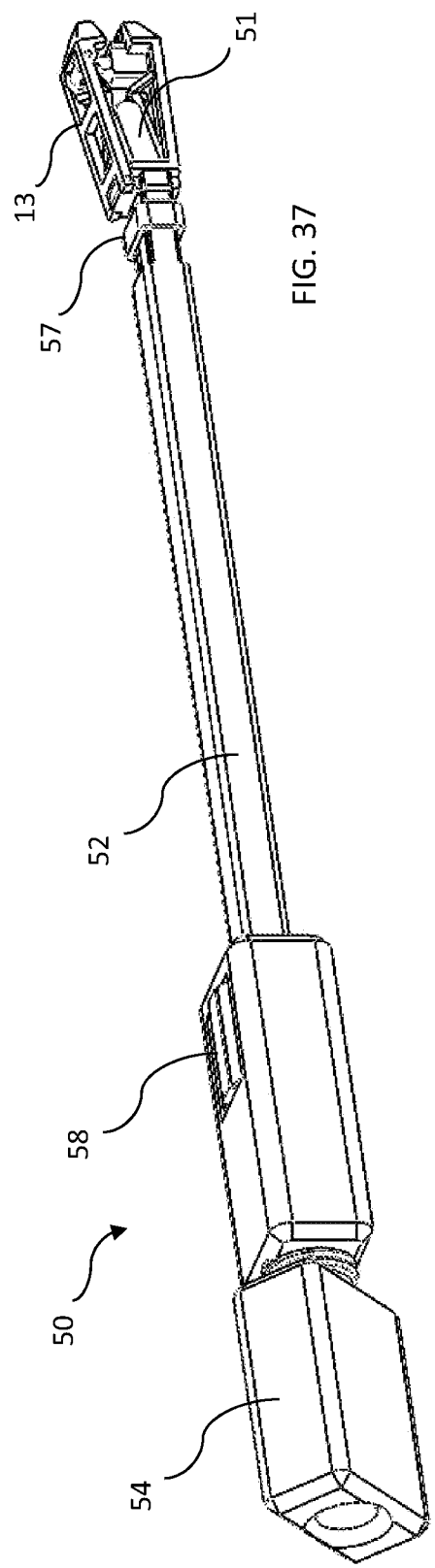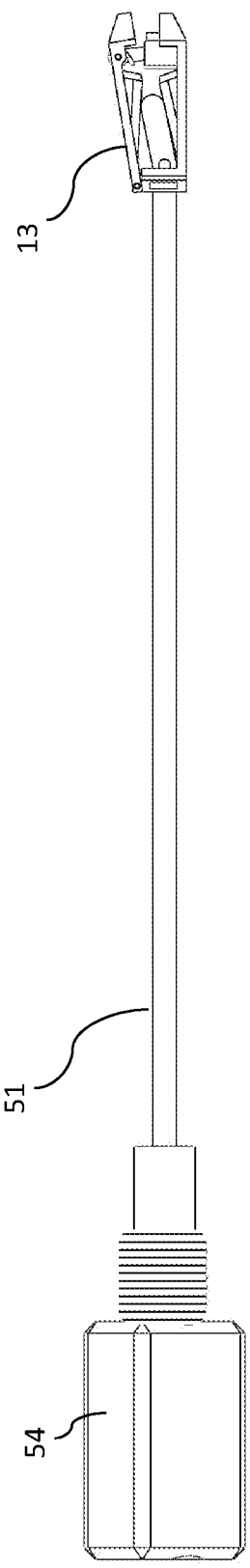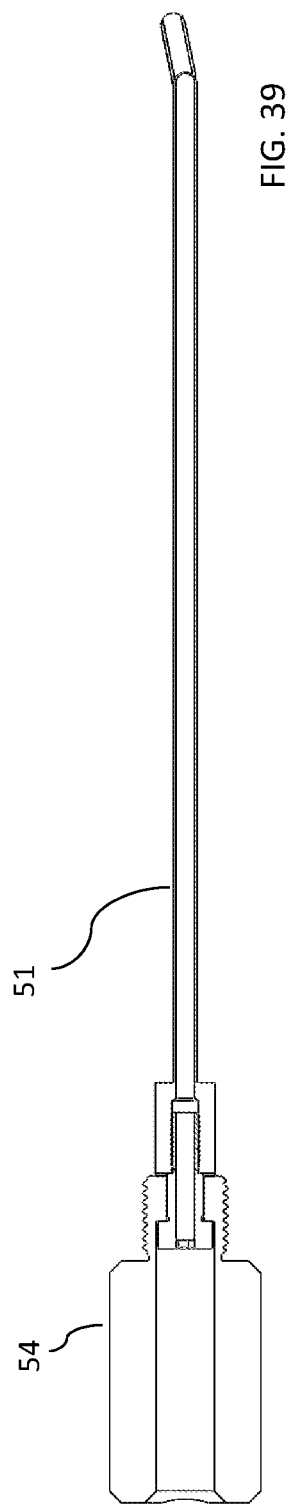
FIG. 37
FIG. 38
FIG. 39

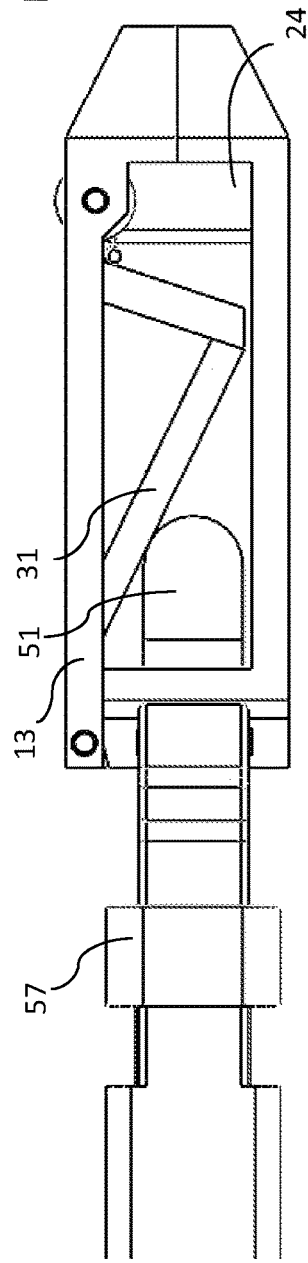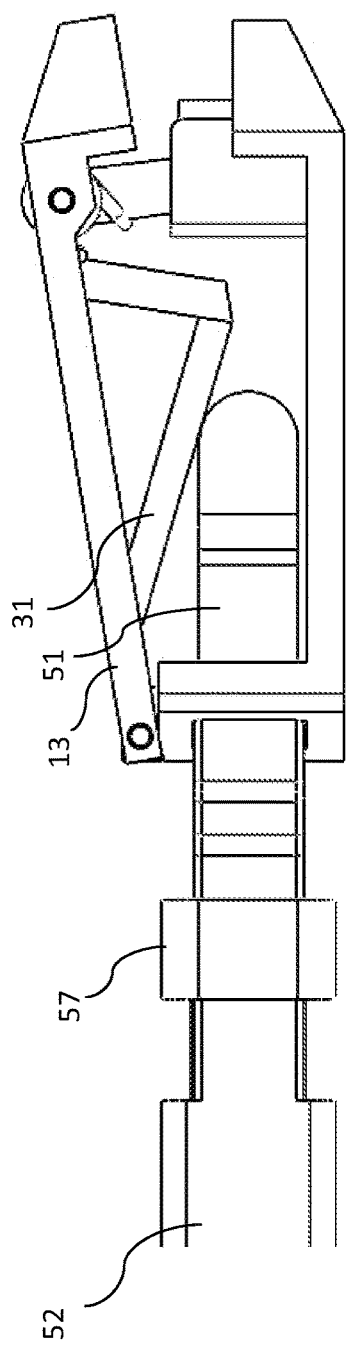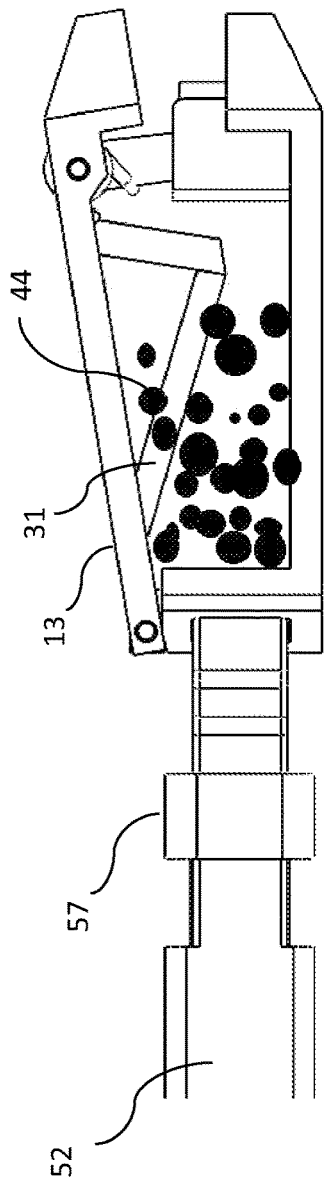

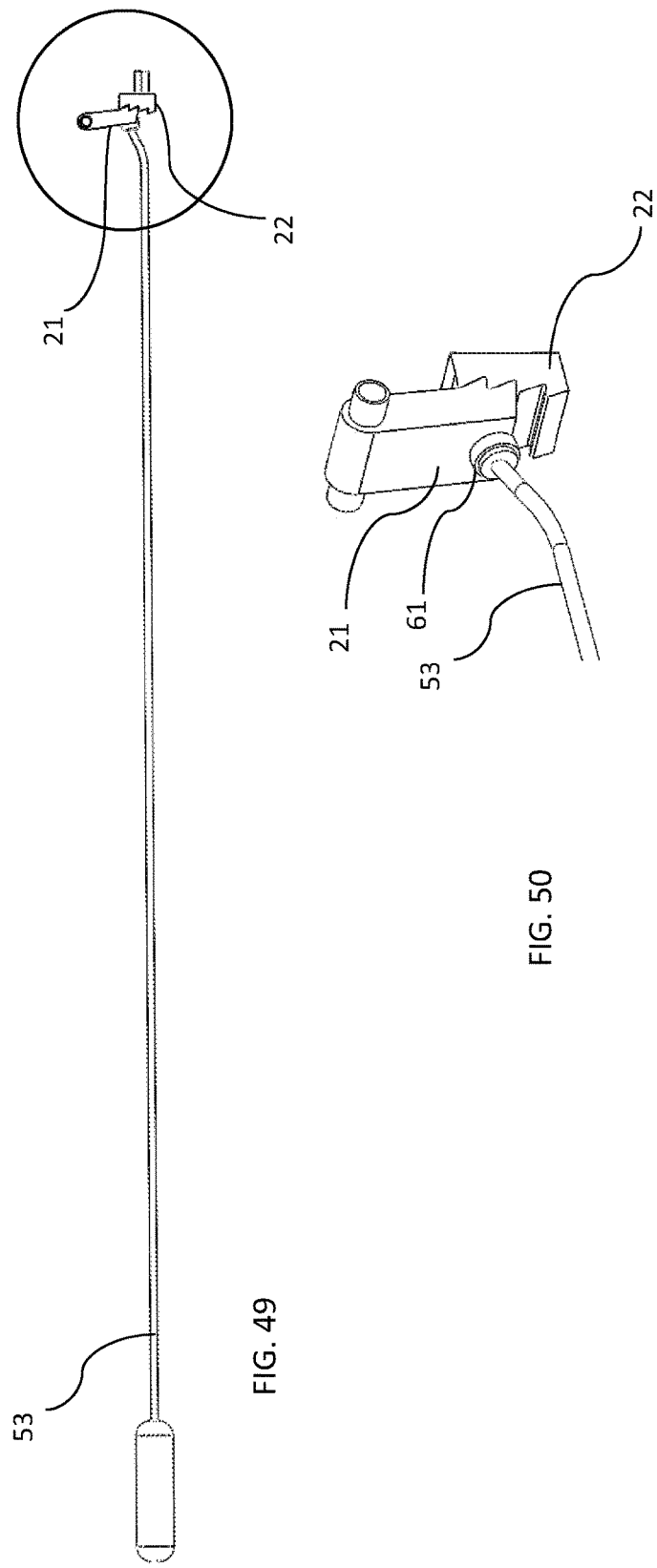
FIG. 49
FIG. 50
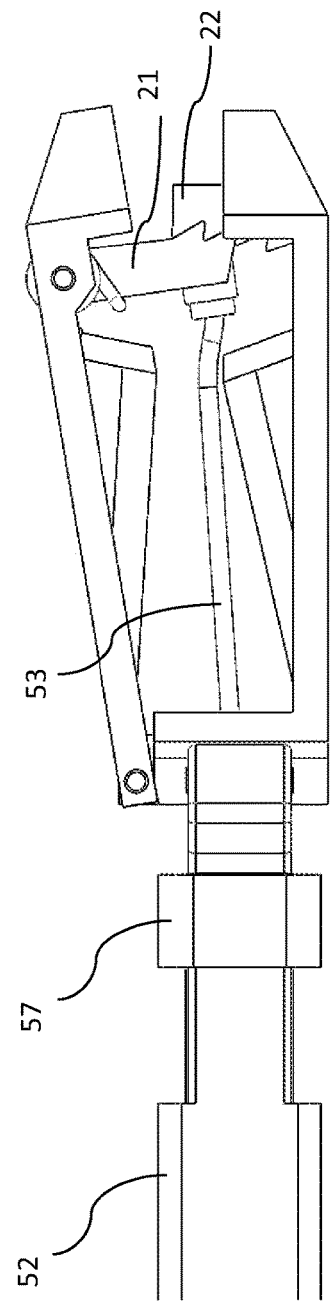
FIG. 51

INTERVERTEBRAL SPACER WITH RAMPED INTEGRAL EXPANSION MECHANISM AND STEPPED LOCKING MECHANISM

FIELD OF INVENTION

The present invention relates generally to intervertebral spacers for orthopedic surgery of the spine. The present invention relates particularly to a spinal implant system in which the spacer has a ramped integral expansion mechanism and a stepped, ratchet-like locking mechanism.

BACKGROUND

Interbody fusion is a type of spine surgery that removes all or part of a degenerated disc from between two adjacent vertebrae in a patient's back. Once the disk is removed, an expandable device is inserted into the disc space between the adjacent vertebrae to forcibly space the vertebrae apart and maintain intervertebral separation. Bone graft material is packed in and around the spacer to provide a scaffolding so that new bone can be formed. The spacer remains between the vertebrae and is anchored to the vertebrae above and below the spacer using anchors such as screws or barbs. The spacer helps maintain spine alignment and intervertebral separation. Additional surgical hardware such as rods, plates, hooks and wire may be used to support the vertebral structure during the healing process. During healing the adjacent vertebra fuse into a single monolithic structure.

Typically the spacer is expanded by using a removable mated tool that engages an expansion mechanism that resides within the body of the spacer. The user uses the tool to incrementally expand the spacer to a proper height to keep the vertebra separated a desired distance. After the spacer is expanded to the proper height, the expansion tool is removed.

Lordosis refers to curvature of the spine that is posteriorly concave. A certain amount of curvature is desired for spine health and patient comfort, but too little curvature or too much curvature may be problematic. When implanting a device between two vertebrae, the lordosis angle of the disk space being repaired must be set appropriately not only for the two surrounding vertebrae, but for vertebrae adjacent to those which may be consequently affected. It would be desirable to have an expandable intervertebral implant to achieve a desired lordosis angle.

Once expanded, it is desirable to lock the spacer at the desired height and angle. The locking mechanism must be strong enough to withstand the compressive forces between the vertebrae and the cage must be robust enough so that it does not collapse or otherwise fail during the patient's lifetime. Strength and durability are vitally important, but making a spacer needlessly robust detracts from the size of the cavity in the spacer for holding bone graft material. A balance is desired.

It is an object of this invention to provide an expandable lordotic interbody spacer system with an integral expansion mechanism and ratchet locking mechanism, which is expanded using a mated expansion tool. It is another object of this invention to maximize the interface between the bone graft material and the patient's vertebrae and tissue.

SUMMARY OF THE INVENTION

An expandable intervertebral spacer system comprises a spacer having an integral expansion mechanism and ratchet locking mechanism and a mated insertion tool. The spacer comprises a top plate and a bottom plate forming a cage surrounding a cavity. The top, bottom, and sides of the cage are open to receive bone graft material. A top ramp extends into the cage from the top plate and, optionally, a bottom ramp extends into the cage from the bottom plate. The top plate and bottom plate are hinged together at the proximal end of the cage, which enables the top plate to be forced apart from the bottom plate so that the plates rest at an angle relative to each other.

The cage is expanded using the mated insertion tool which inserts a pushrod into an opening in the proximal end of the cage against the ramp or ramps in the cage. As the pushrod is extended deeper into the cage, the end of the pushrod cooperates with the ramp or ramps to force the distal ends of the plates apart so that the top and bottom plates are no longer parallel.

A stanchion locks the plates apart a desired distance and thus at a desired angle. The stanchion is made of a top rotatable post and a bottom stationary post that cooperate to lock the top plate at a desired angle from the bottom plate with a ratchet-like locking mechanism. The posts have saw-teeth that intermesh and the posts are biased against each other with a torsion spring. Optionally, the stanchion is surrounded by a sheath to prevent bone particles and other debris from interfering with the mating of the saw teeth.

In some embodiments, the insertion tool is configured to cooperate with the movable post to unlock the saw teeth and allow the spacer to return to its unexpanded state.

BRIEF DESCRIPTION OF THE DRAWINGS

FIG. 32 is a top cross section view of the clamp arms before the tabs are clamped to a cage.

FIG. 33 is a top cross section view of the clamp arms after the tabs are clamped to a cage.

FIG. 34 is a top perspective view of the open clamp arms approaching a cage.

FIG. 35 is a top perspective view of the clamp arms in position to clamp the cage.

FIG. 36 is a top perspective view of the clamp arms clamped to the cage.

FIG. 37 is a top perspective view from the proximal end of the inserter and a spacer of the first embodiment.

FIG. 38 is a cut-away side view of the inserter showing the pushrod and the spacer of the first embodiment.

FIG. 39 is a cross-section view of the insertion device of FIG. 37 without the spacer.

FIG. 46 is a side view of the pushrod partially extending into the spacer of the second embodiment.

FIG. 47 is a side view of the pushrod extending into the spacer of the second embodiment far enough to expand the spacer a desired height.

FIG. 48 is a side view of the pushrod withdrawn from the spacer of the second embodiment, leaving it in a locked expanded desired height, and bone graft material.

FIG. 49 is a side view of an unlocking cable attached to the ratchet locking mechanism in the spacer of the second embodiment.

FIG. 50 is an enlarged view of the portion circled in FIG. 49, showing the cable attached to the ratchet locking mechanism.

FIG. 51 is a side view of the unlocking cable attached to the ratchet locking mechanism in the spacer of the second embodiment.

DETAILED DESCRIPTION OF THE INVENTION

This expandable intervertebral spacer system comprises a spacer 10 having an integral expansion mechanism and integral ratchet locking mechanism and a mated insertion tool. The spacer 10 is inserted into a patient's body in an unexpanded form using a mated removable insertion tool 50, which further comprises a pushrod 51 and, optionally, an unlocking mechanism.

Figure 1:
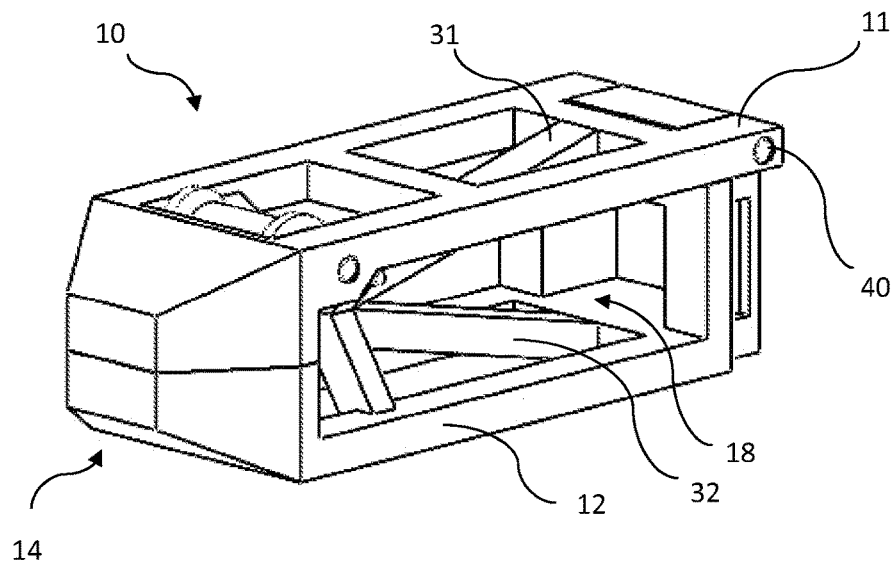
FIG. 1 is a top perspective view from the distal end of a first embodiment of a spacer in unexpanded configuration.
Figure 2:
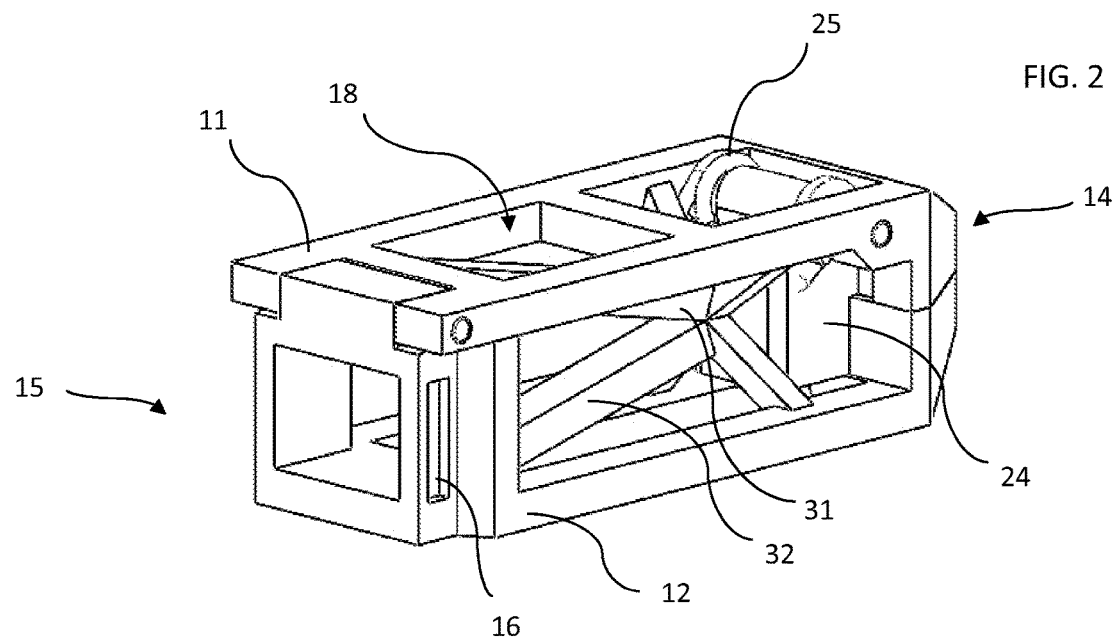
FIG. 2 is a top perspective view from the proximal end of the spacer in FIG. 1.
Figure 3:
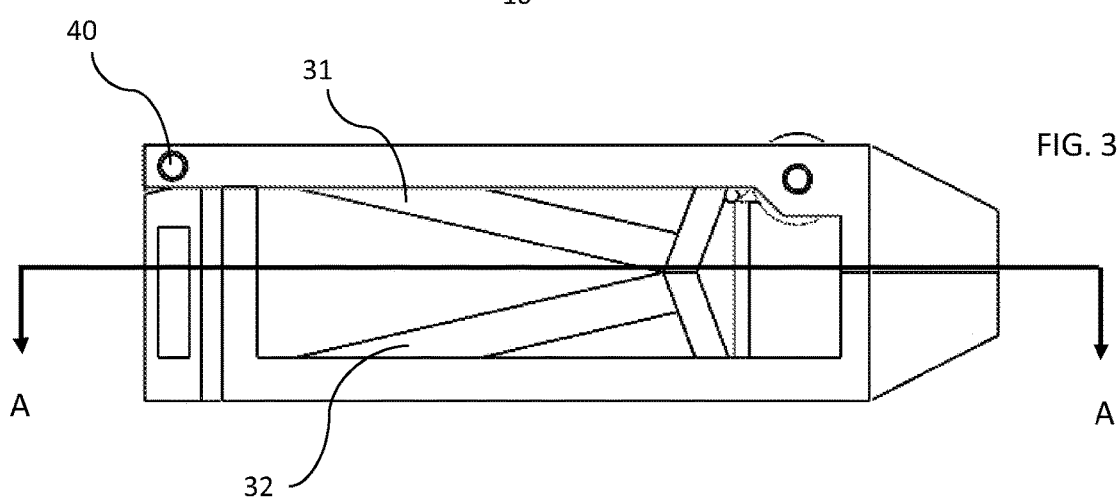
FIG. 3 is a side view of the spacer of FIG. 1.
Figure 15:
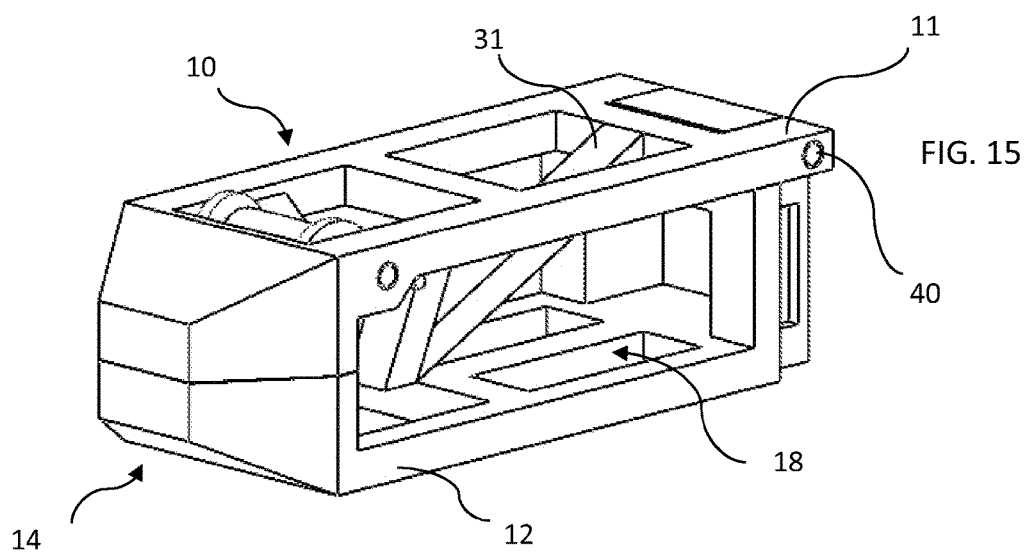
FIG. 15 is a top perspective view from the distal end of a second embodiment of a spacer in unexpanded configuration.
Figure 16:
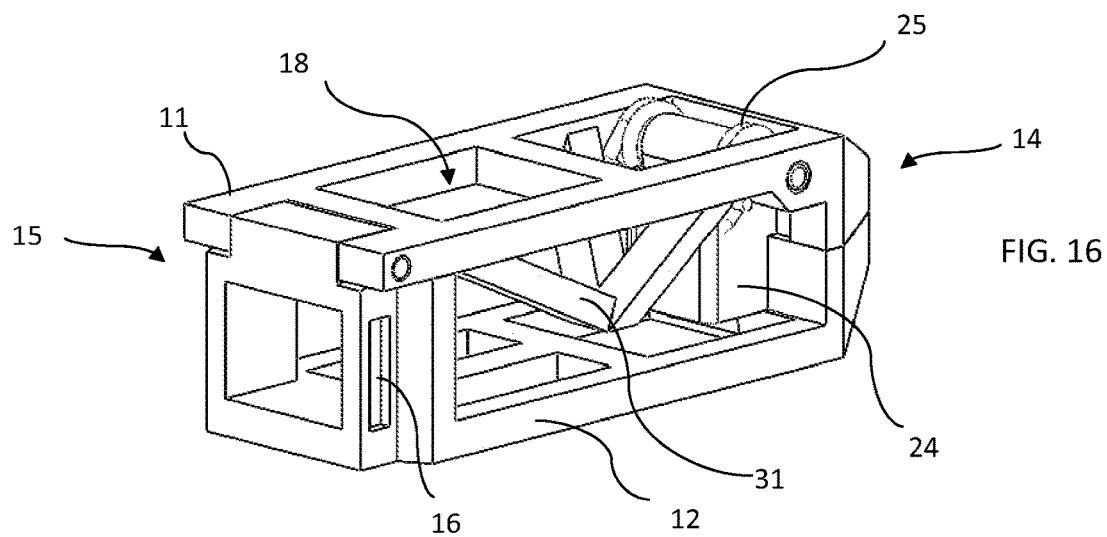
FIG. 16 is a top perspective view from the proximal end of the spacer in FIG. 15.
Figure 17:
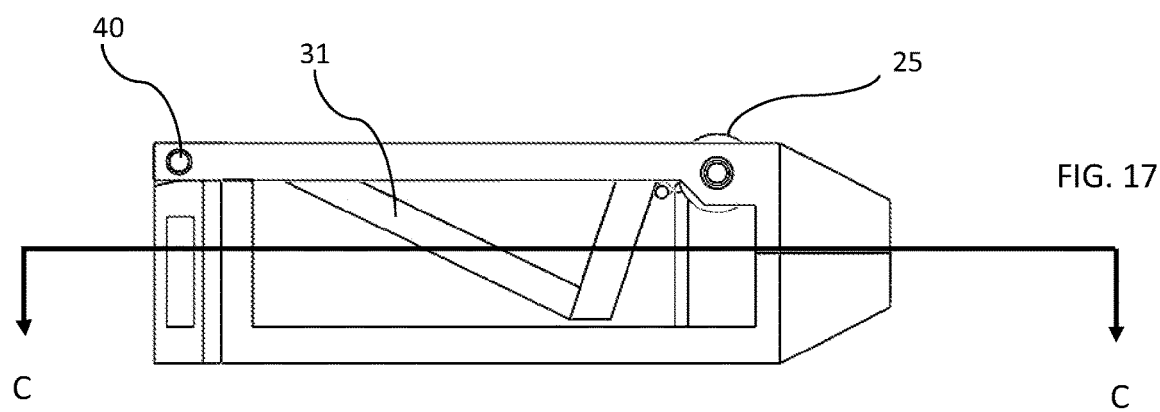
FIG. 17 is a side view of the spacer of FIG. 15.
Figure 18:
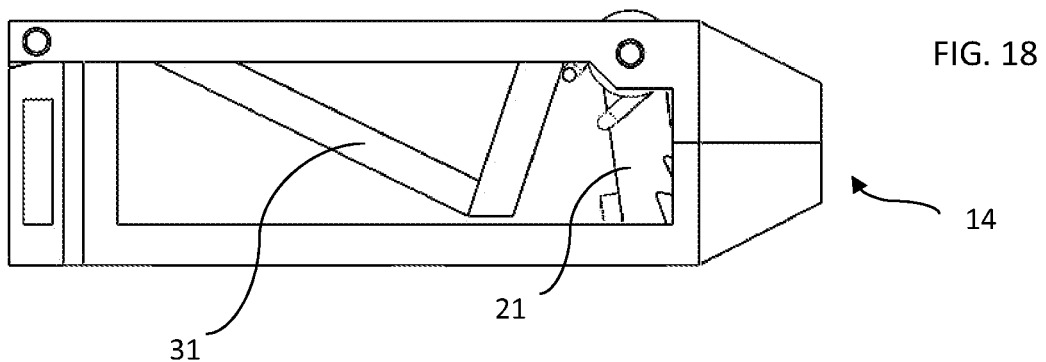
FIG. 18 is a side view of the spacer of FIG. 15, shown without the sheath.
Figure 19:
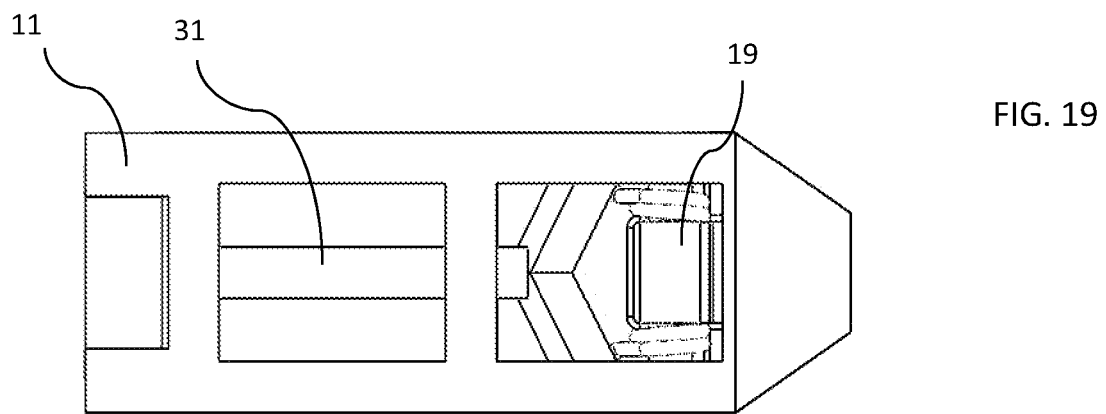
FIG. 19 is a top view of the spacer of FIG. 15.
Figure 20:
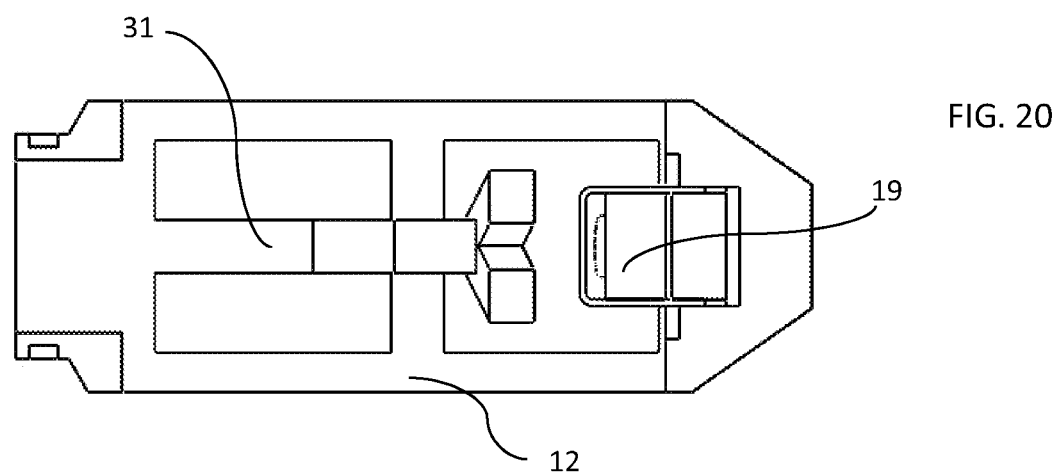
FIG. 20 is a top view of the spacer of FIG. 15 taken along line C-C of FIG. 17.
Figure 21:
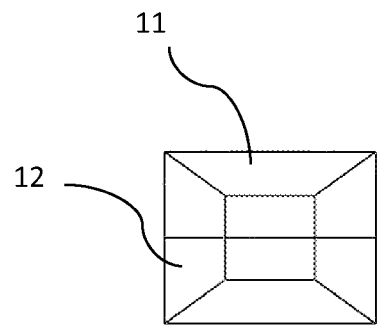
FIG. 21 is an end view of the distal end of the spacer of FIG. 15.
Figure 28:
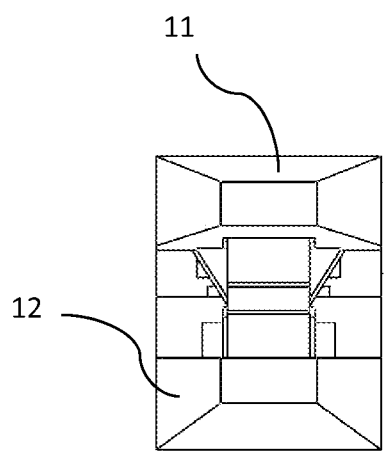
FIG. 28 is an end view of the distal end of the spacer of FIG. 22.
Figure 22:
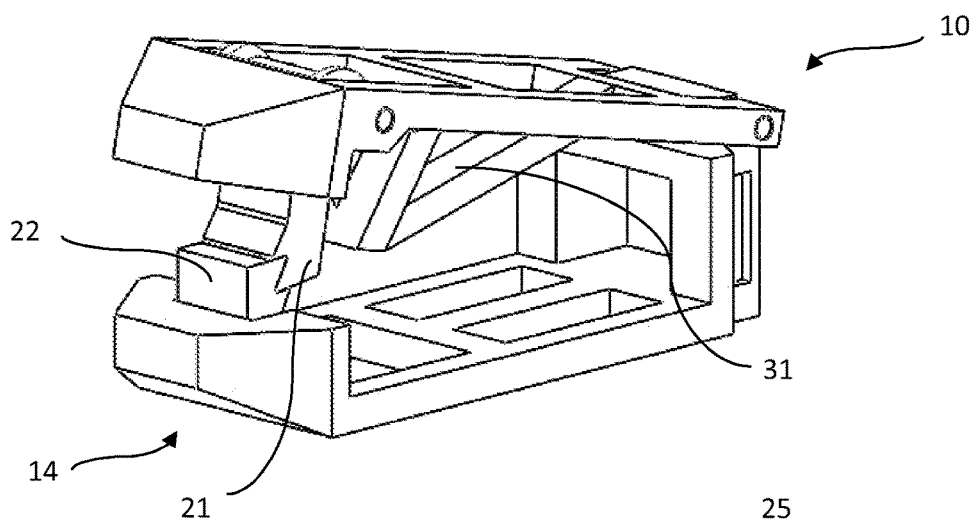
FIG. 22 is a top perspective view from the distal end of the spacer of FIG. 15 in an expanded configuration.
Figure 23:
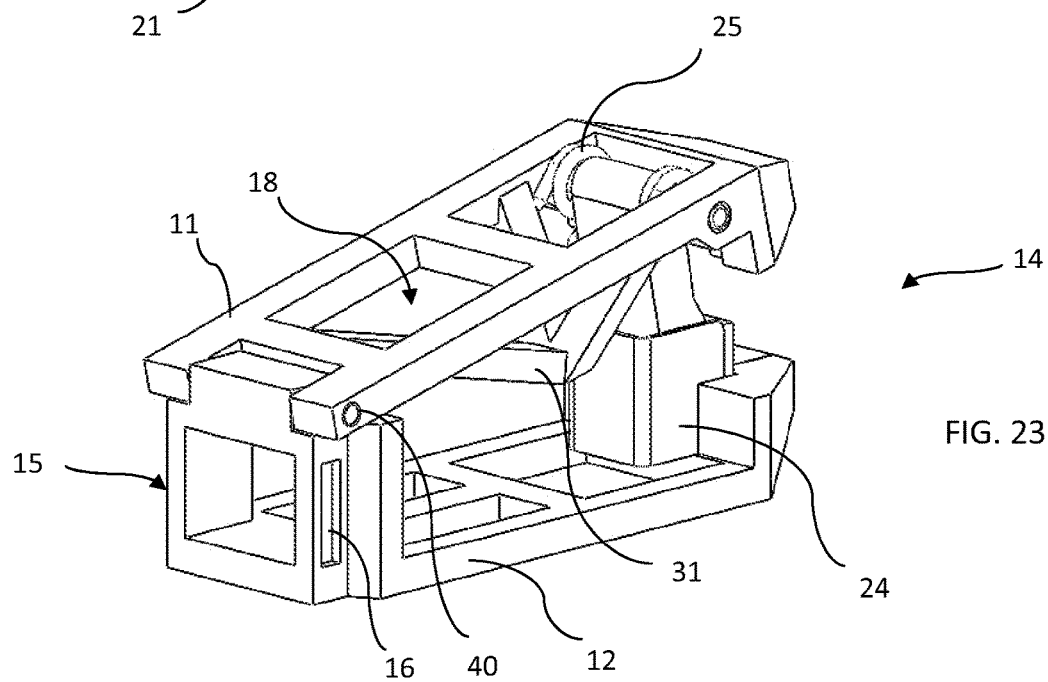
FIG. 23 is a top perspective view from the proximal end of the spacer in FIG. 22.
Figure 24:
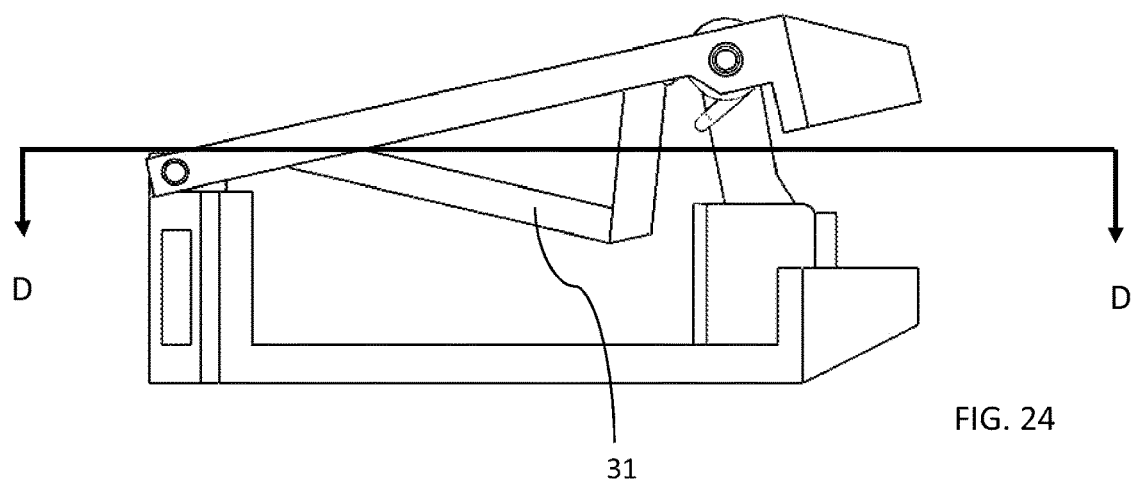
FIG. 24 is a side view of the spacer of FIG. 22.
Figure 25:
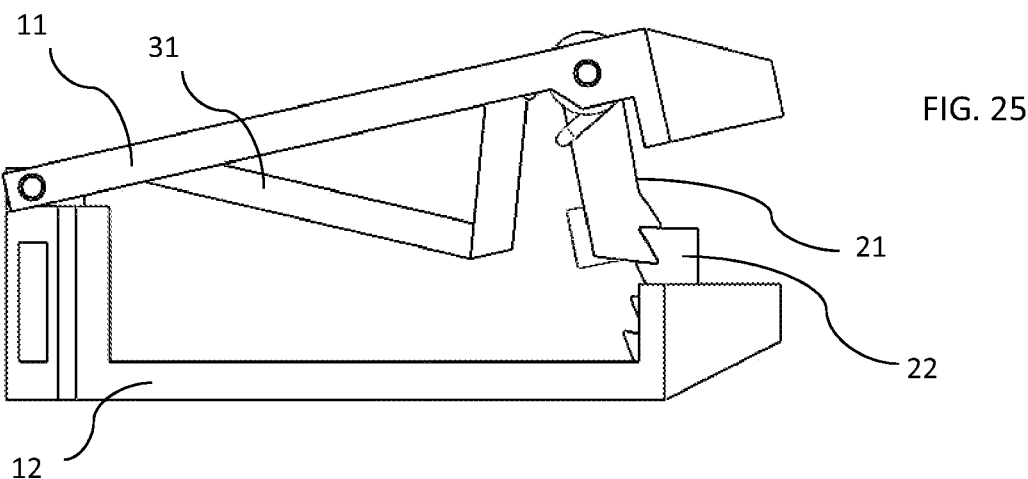
FIG. 25 is a side view of the spacer of FIG. 22, shown without the sheath.
Figure 26:
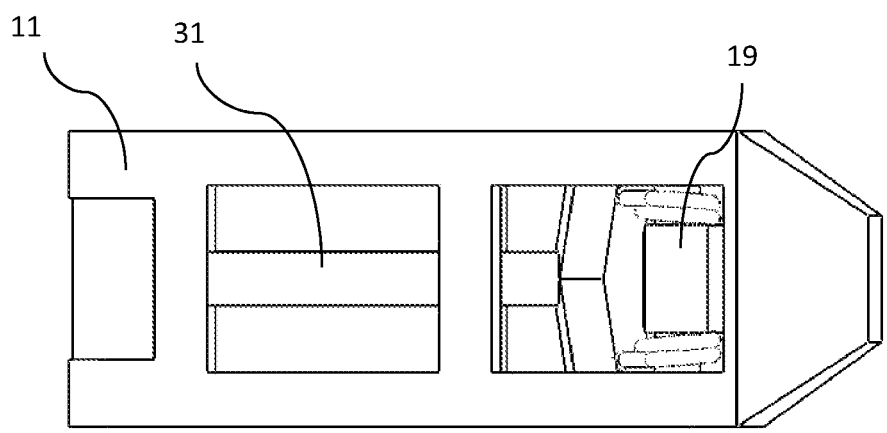
FIG. 26 is a top view of the spacer of FIG. 22.
Figure 27:
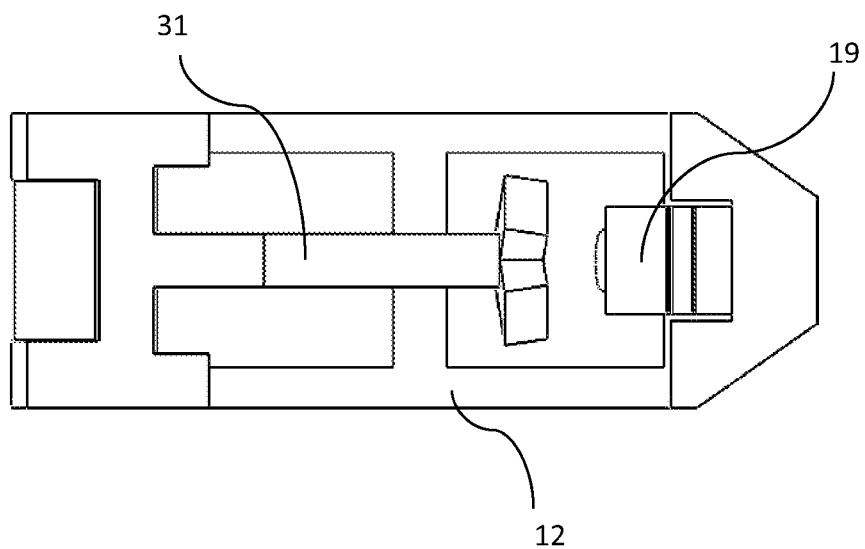
FIG. 27 is a top view of the spacer of FIG. 22 taken along line D-D of FIG. 24.
Figure 31:
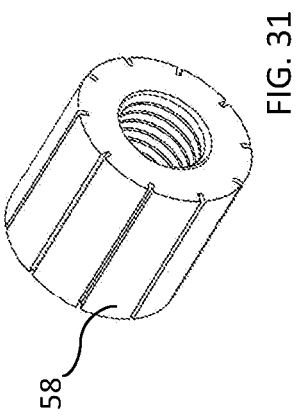
FIG. 31 is a perspective view of threaded clamp nut.
Figure 60:
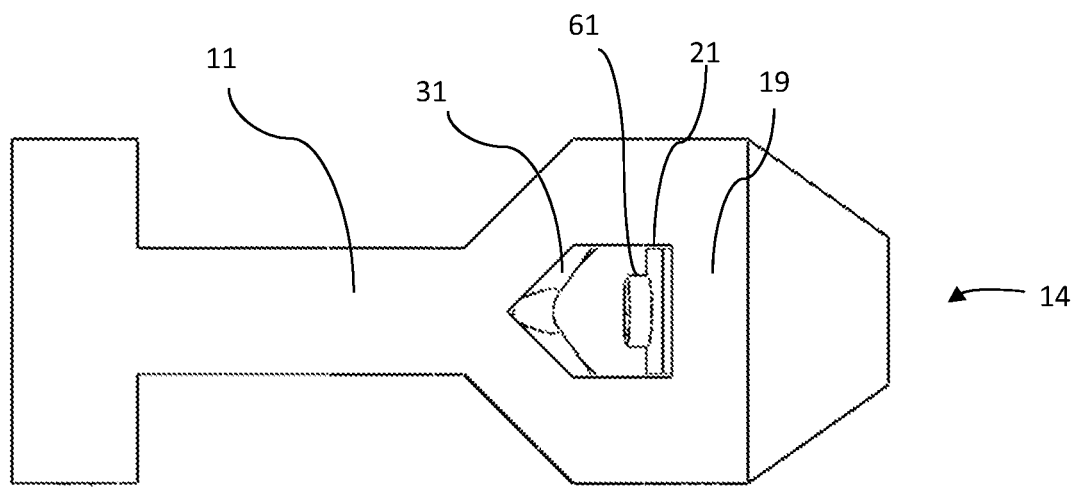
FIG. 60 is a top view of a third embodiment of the spacer.
Figure 61:
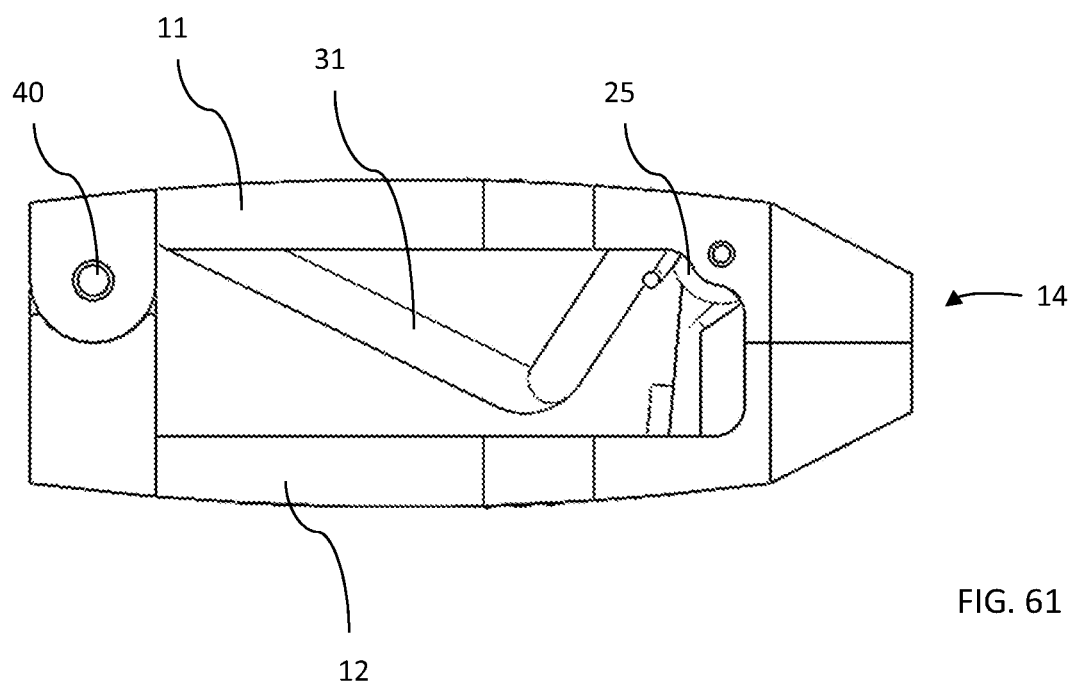
FIG. 61 is a side view of the spacer of FIG. 60.

The spacer comprises a top plate 11 and a bottom plate 12 forming a cage 13 surrounding a cavity. The top, bottom and sides of the cage 13 have openings, referred to herein as cutouts 18, to permit bone graft material 44 to be more easily packed into the cavity between the plates and thereby increase the surface exposure of the graft material to the patient's vertebrae. In some embodiments the cage is substantially rectangular, as shown in FIGS. 1 and 15. In other embodiments the cage 13 is barbell shaped, with the top plate 11 and bottom plate 12 comprising a center spine connecting the proximal hinge area with the distal ratchet area. See FIGS. 60-61.

The proximal end 15 of the cage 13 has clamping slots 16 which are grasped by an insertion tool, as explained in more detail below. The distal end 14 of the spacer 10 is the leading end when inserting the device between vertebrae and is typically rounded for ease of insertion. The distal end 14 is typically solid so that no debris from the patient's body enters the cavity during insertion, but optionally the distal end 14 may also have cutouts. The proximal end 15 of the spacer 10 is open to accommodate the insertion tool. This opening is considered a cutout 18 of the device. The bone graft material packed in and around the spacer provides a scaffolding so that new bone can be formed. The bone graft material may be cancellous or cortical bone, or both, and is preferably autograft or allograft tissue.

The cage 13 contains one or more ramps. In one embodiment, each ramp has first portion connected to a second portion, forming a V-shape or solid wedge extending from the plate the ramp is attached to. The first portion of the ramp is angled into the cage from the proximal end toward the distal end of the cage. The second portion of the ramp is angled away from the plate. In yet other embodiments, the ramp has a single leg that is angled from the proximal end toward the distal end of the cage.

The ramp is preferably V-shaped, with no material under the apex of the V, to minimize weight and maximize cage volume for bone graft material. In other embodiments, the ramps are solid wedges with material filling in the V to form a solid triangle. Instead of a sharp point at the apex of the ramp, the apex may be rounded in more of U shape. With each ramp extending into the cage from the top or bottom plate, or both, as opposed to extending from either side of the cage, the top, bottom and sides of the cage have cutouts 18, as opposed to being solid. Cutouts 18 in the in the top, bottom and all sides of the cage 13 enables bone graft material to be packed in through each surface, and exposes that material to the patient's vertebra. Cutouts in the top, bottom and all sides of the cage maximizes the exposure of the bone graft material to patient tissue.

The ramps extend into the cage from the top and bottom of the cage, as opposed to extending into the cage from the sides of the cage. In a first embodiment, a top ramp 31 extends into the cavity from the top plate 11, and a bottom ramp 32 extends into the cavity from the bottom plate 12. See FIGS. 1-14. Each ramp may be as long as the entire length of the cage, from the proximal end to the distal end or, as shown in FIGS. 1-13, the ramps are shorter than the entire length of the cage 13. The ramps are preferably equidistant from the longitudinal centerline of the cage, whether close to the centerline or at the periphery of the cage.

The top plate 11 and bottom plate 12 are connected together at the proximal end of the cage 13 at a hinge 40, which enables the top plate 11 to be forced apart from the bottom plate 12 at an angle, as explained in more detail below. As shown the figures, the hinge 40 is typically a pin hinge that fits in a barrel slot of the top plate and bottom plate to hold the plates together and allow them to swing away from each other. Alternatively, the plates can be hinged together with two pivot hinges on either side of the proximal end of the cage.

In a second embodiment, only one ramp extends into the cavity from either the top or bottom plate. In a preferred embodiment shown in FIGS. 15-28, a top ramp 31 extends into the cavity from the top plate 11. The top ramp 31 may be as long as the entire length of the cage, from the proximal end to the distal end or, as shown the embodiment of FIGS. 15-27, the ramp is shorter than the entire length of the cage 13. The single ramp is on the longitudinal centerline of the cage to encourage uniform lifting and limited side-to-side roll of the top plate during expansion.

In another embodiment, two ramps extend into the cavity from either the top or bottom plate. The ramps are equidistant from the longitudinal centerline of the cage, whether close to the centerline or at the periphery of the cage.

Figure 54:
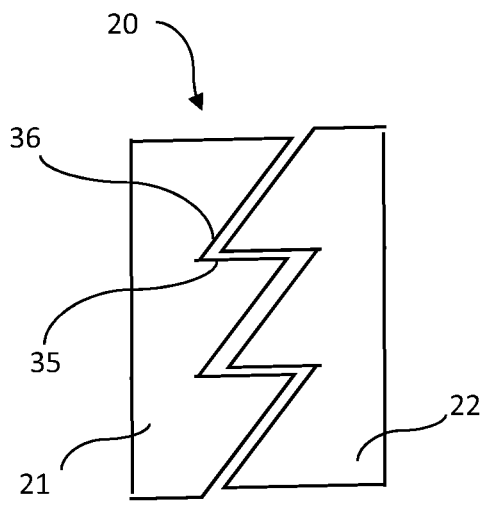
FIG. 54 is a schematic illustration of a portion of a stanchion.
Figure 55A:
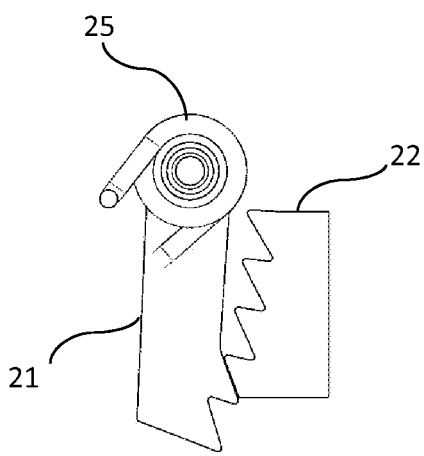
FIGS. 55A-D are side views of the locking mechanism, each with different number of saw-teeth engaged.
Figure 55B:
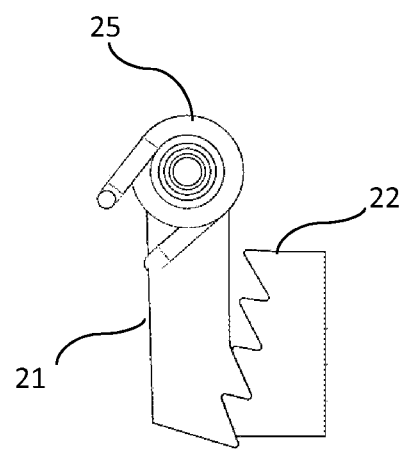
Figure 55C:
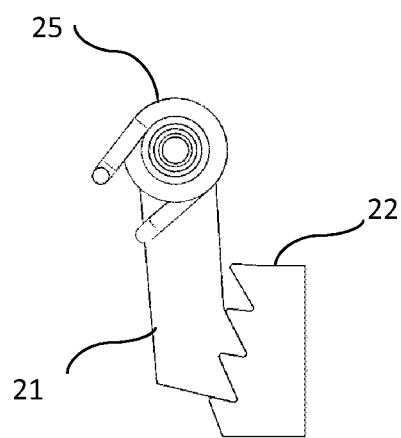
Figure 55D:
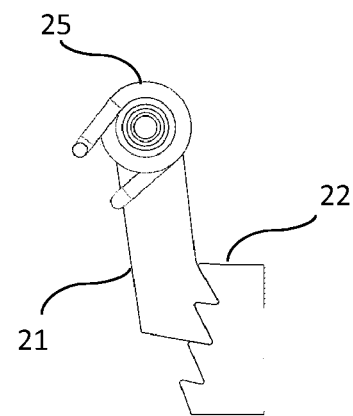

The top and bottom plates 11, 12 are separated and held apart by a ratcheting locking mechanism 19. The locking mechanism 19 uses at least one stanchion 20 to provide robust and balanced support between the plates. Each stanchion 20 comprises two saw-tooth posts 21, 22 that move relative to one another and cooperate to lock the top plate 11 at a desired angle from the bottom plate 12. See FIGS. 54-55. One saw-tooth post 21 is movable, rotating toward and away from the other saw-tooth post 22. Saw-tooth post 22 is stationary. Preferably the movable post 21 protrudes from the top plate 11 into the cage 13 and the stationary post 22 protrudes from the bottom plate 12 into the cage 13.

Figure 57:
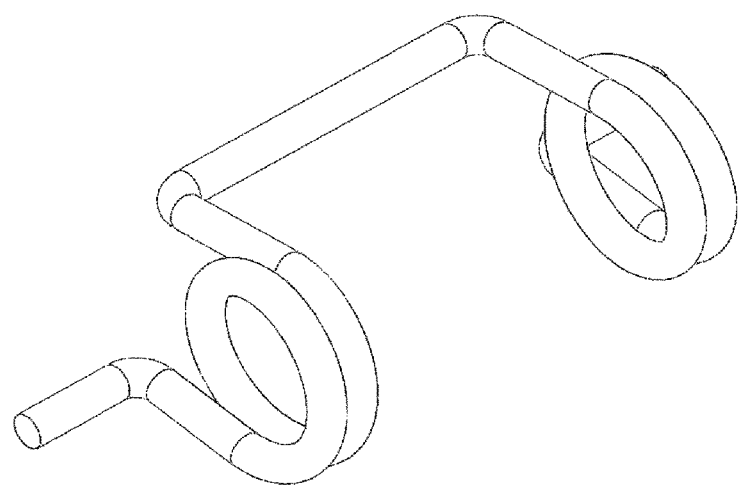
FIG. 57 is a perspective view of a torsion spring.

The posts 21, 22 are biased against each other with a helical torsion compression spring 25 that exerts a torque or rotary force on the movable post 21 around the axis of the torsion spring. A torsion spring is illustrated in FIG. 57. The torsion spring 25 forces the movable post 21 against the stationary posts 22 in the stanchion 20 when the torsion spring is at rest. As the top and bottom plates are forced apart, the torsion spring is compressed and the posts 21, 22 are forced apart and unlocked. When the top and bottom plates are separated to the desired distance, the torsion spring relaxes, thus forcing the saw teeth of the posts to intermesh again, which locks the top and bottom plates apart at the desired distance. Certain figures show embodiments in which the coils of the torsion spring 25 extend slightly above the top plate 11, maximizing the open volume of the cage 13. In other embodiments, the torsion spring 25 is disposed lower in the cage 13 so that the spring coils are flush with the top surface of the top plate 11 or even below it.

In an alternative embodiment, in lieu of the torsion spring biasing the posts 21, 22 against each other, a linear spring disposed perpendicularly between the top plate 11 and bottom plate 12 biases the plates 11, 12 apart. This in turn forces the teeth of the posts 21, 22 against each other, locking them in place.

Figure 56:
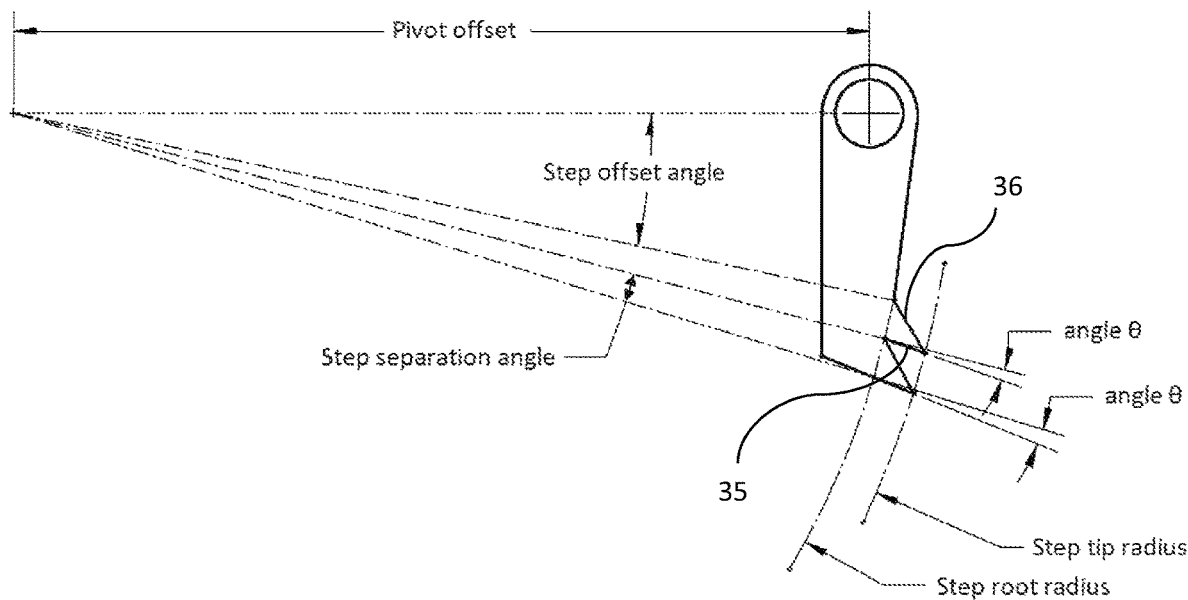
FIG. 56 illustrates effect of saw teeth that are not at 90 degrees to the post.

Each saw tooth is generally triangular with one side of the triangle extending away from the post at an angle of about 90-106 degrees. This portion of the tooth is referred to herein as the horizontal edge 35. In one embodiment, the horizontal edge is at a right angle to its post, parallel to the top and bottom plates 11, 12. See FIG. 54. In another embodiment, the horizontal edge is greater than 90 degrees to the post, and angle theta shows the difference from perpendicular. See FIG. 56. Angle theta denotes an angular offset from the line between the center-to-root line and root-to-tip line, where the root is the point at which the step attaches to the post. The other edge of the saw tooth is at a complementary angle to its post, referred to herein as the angled edge 36. The teeth of one post intermesh with the teeth of the neighboring post. When the saw teeth are engaged, the horizontal edge 35 of each tooth sits against a horizontal edge 35 of one or more teeth on the opposing post. This holds the top and bottom plates stationary relative to each other, locking the plates to each other. The greater the angle theta of the horizontal edge 35 to the post, the greater the force required to separate the posts 21, 22 from each other. When expanding the cage with horizontal edge at angles more than 90 degrees, the ramp has to be forced open farther than if the horizontal edge is at 90 degrees to get over the lip of the step. Then, the post slides down so that the teeth intermesh. Posts intermeshed with theta angles greater than zero create an interlocking force on the steps which pushes them together and increases the security of the locking mechanism.

The asymmetrical shape of the saw teeth enables the plates to be forced apart incrementally, one saw tooth at a time, in a ratchet-like motion. The posts 21, 22 are forced apart from each other when the top and bottom plates are forced away from each other with the expansion mechanism, due to the cooperative shape of the saw teeth. As the top plate is forced away from the bottom plate, as explained in more detail below, the angled edges of the teeth of the top post slide against the angled edges of the teeth of the bottom post, forcing the top post to rotate away from the bottom post in an amount sufficient to release the horizontal edges of the formerly intermeshed teeth.

The height of the saw teeth determines the distance of each increment of separation between the plates: the smaller the tooth height, the finer the degree of separation for each increment. The number of teeth and height of the teeth determine the maximum distance the plates can be separated. At maximum expansion, preferably a minimum of two teeth are engaged on each stanchion.

The width of the stanchion 20 varies depending on the size of the spacer, with the width of the stanchion ranging from about 2 mm-6 mm. In one example, the horizontal edge 35 of each saw tooth is 1.5 mm deep and 4 mm wide. Assuming two teeth are engaged per stanchion, this provides for a minimum total contact area of 6 mm² (2 teeth×1.5 mm deep×4 mm wide). Given a compressive strength of titanium alloy to be 850 MPA, the load to failure is 10,200N. Thus the locking mechanism can withstand the compressive forces between the vertebrae and the cage so that the spacer does not collapse or otherwise fail during the patient's lifetime.

Preferably a single stanchion is used at the distal end to lock the plates apart, to minimize the number of moving parts and maximize the size of the teeth and consequently compressive strength. In some embodiments two stanchions may be used, such as one at each corner of the distal end of the cage.

Optionally, a sheath 24 surrounds each stanchion or the whole locking mechanism to prevent bone particles and other debris from interfering with the mating of the saw teeth. The sidewall thickness of the sheath 24 is preferably less than 1 mm.

Figure 29:
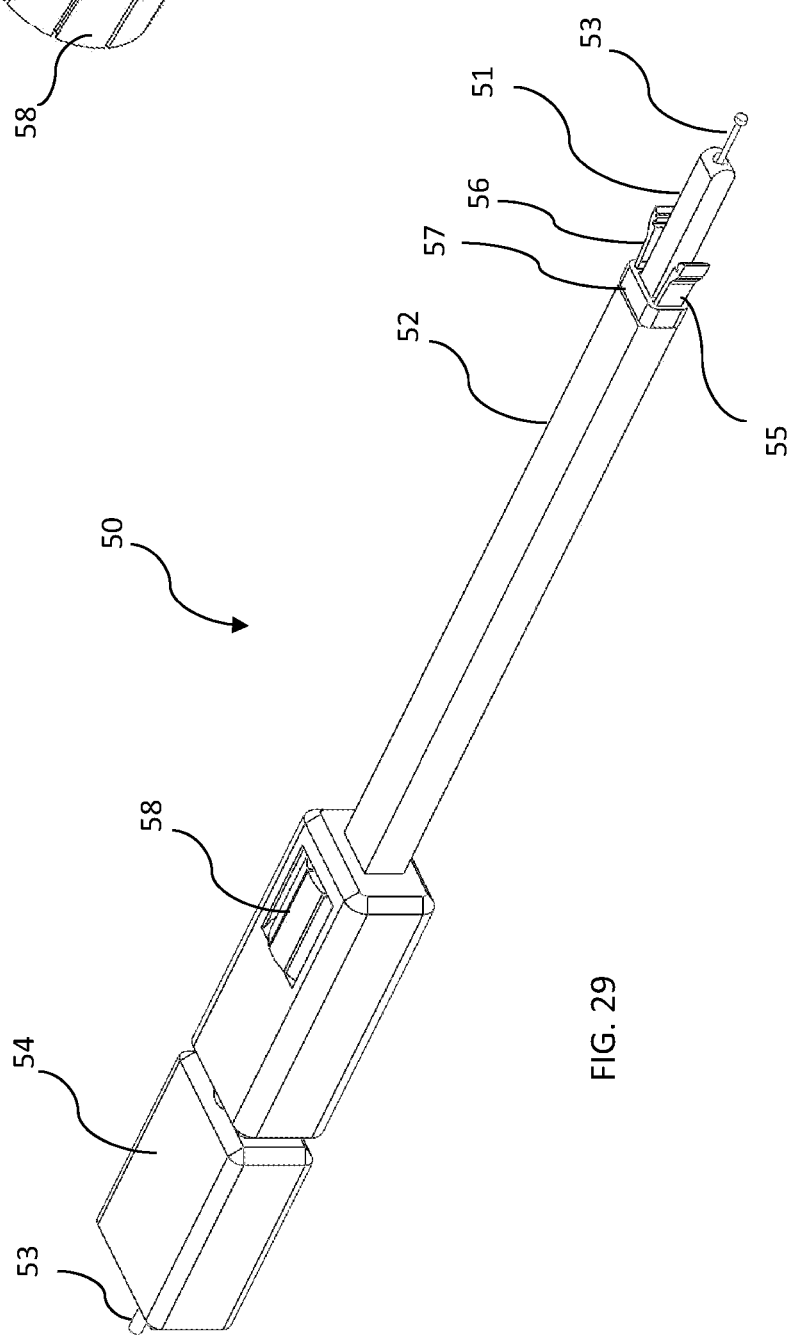
FIG. 29 is a perspective view of an insertion tool.
Figure 30:
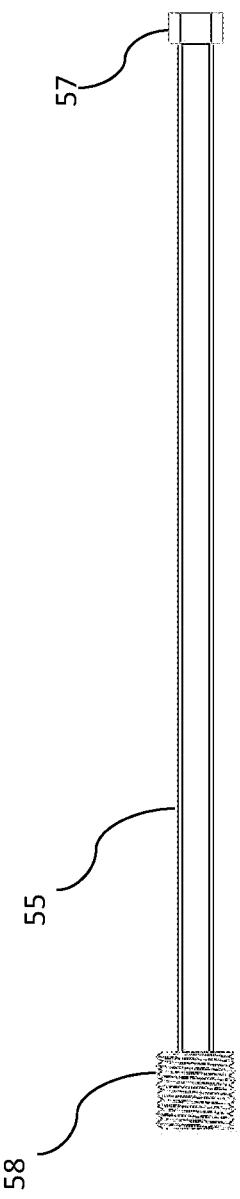
FIG. 30 is a side view of the shaft assembly and clamp collar of the inserter.

The spacer 10 is inserted into the patient's body in an unexpanded form using a removable insertion tool 50. See FIGS. 29 and 37. The insertion tool 50 comprises clamping arms 55 and 56, a pushrod 51 and, optionally, an unlock cable 53, inside a hollow shaft 52, which serves as a lumen through which the insertion tool components work on the spacer. In a preferred embodiment, the pushrod 51 sits between and concentrically within the clamp arms inside the hollow shaft. The unlock cable may sit aside the clamp arms or between them in the hollow shaft, but preferably the unlock cable passes through the central lumen of the insertion tool.

The clamping arms 55 and 56 are shown in FIGS. 29-36. The ends of the clamping arms are tabs that fit in the clamp slots 16 on the end of the proximal cage 13 so that the insertion tool can securely hold on to the cage during insertion and release it once inserted. The clamp arm tabs are inserted into the clamp slots, and closed toward each other by moving the clamp collar 57 toward the end of the clamp arms. The clamp collar 57 is moved over the clamp arms by rotating a threaded cylinder 58. Rotation of the cylinder 58 in a first direction moves the collar 57 toward the cage, tightening the tabs in the clamp slots of the cage. Rotation of the cylinder 58 in the reverse direction moves the collar 57 away from the cage, loosening the tabs from the slots of the cage.

Once the cage is clamped to the insertion tool, the cage is inserted into the patient between two vertebrae. The cage is moveable between a collapsed configuration in which the top plate and bottom plate are parallel and an expanded configuration, wherein the top plate and bottom plate are not parallel. When expanded, the plates 11, 12 are separated at the distal end, forming an opening, which is considered a cutout 18 herein. Expansion is accomplished by extending the pushrod 51 into the cage 13 by turning a threaded handle 54. The pushrod moves through the hollow shaft 52 toward the cage without rotating. The distal end of the pushrod is wide enough to cooperate with the ramp or ramps in the cage, but narrow enough to fit in the aperture in the proximal end of the cage. The distal end of the pushrod is preferably round, but may be pointed or flat.

Figure 40:
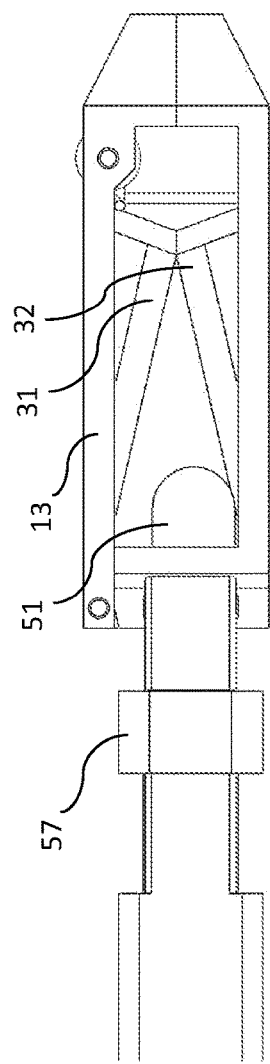
FIG. 40 is a side view of the pushrod partially extending into the spacer of the first embodiment.
Figure 41:
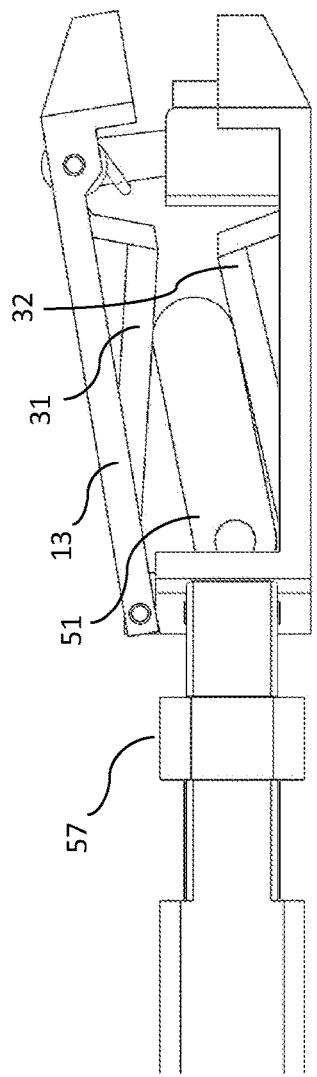
FIG. 41 is a side view of the pushrod extending into the spacer of the first embodiment far enough to expand the spacer a desired height.
Figure 42:
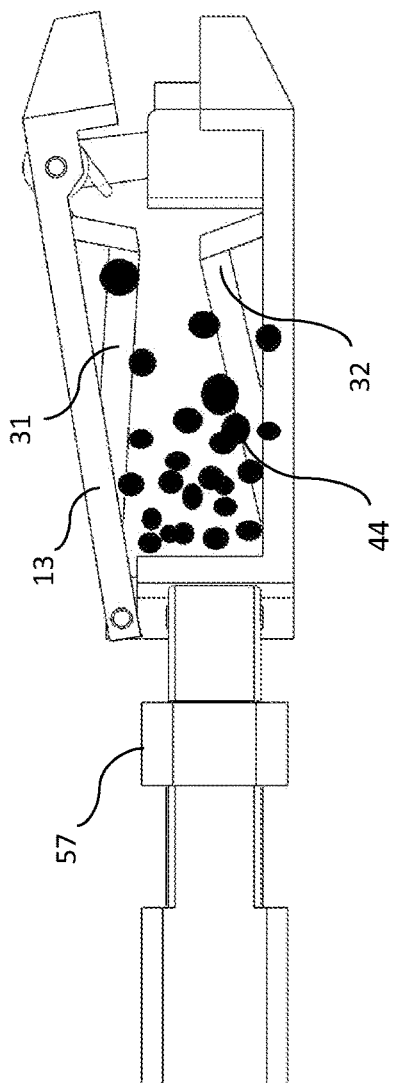
FIG. 42 is a side view of the pushrod withdrawn from the spacer of the first embodiment, leaving it in a locked expanded desired height, and bone graft material.

The pushrod 51 is mated to each embodiment. For the first embodiment of the spacer having two ramps, the pushrod 51 is articulated at the end, most easily seen in FIGS. 38 and 39. As the pushrod 51 is extended into the cage 13, the articulated tip rides up the bottom ramp 32 between the top and bottom ramps, forcing the top and bottom plates apart. See FIGS. 40-41. Once the top and bottom plates are resting at the desired angle, the pushrod 51 is withdrawn. See FIG. 42. Bone graft material 44 is then packed into the spacer.

Figure 43:
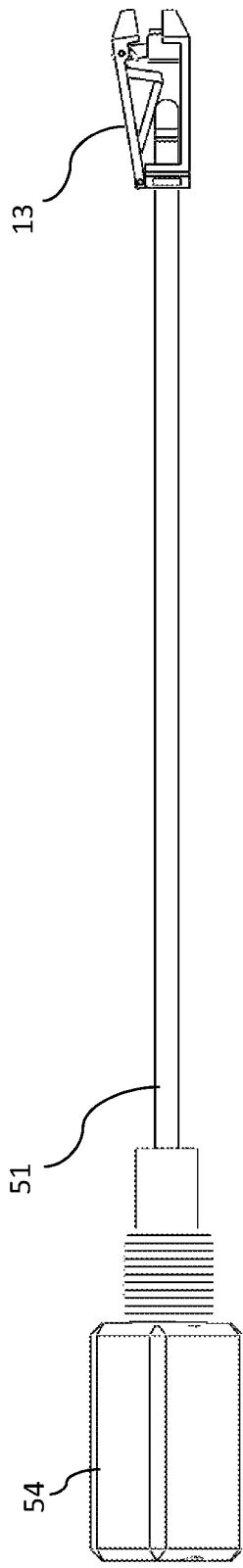
FIG. 43 is a side view of the pushrod and the spacer of the second embodiment.
Figure 44:
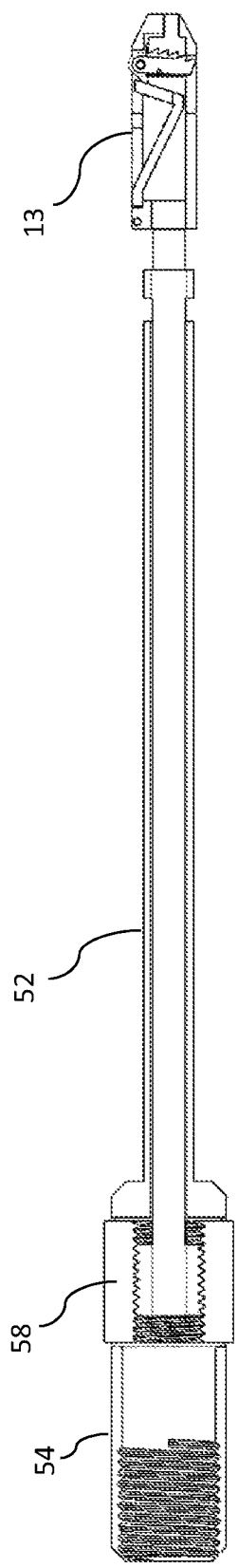
FIG. 44 is a cross section view of the insertion tool and the spacer of the second embodiment.
Figure 45:
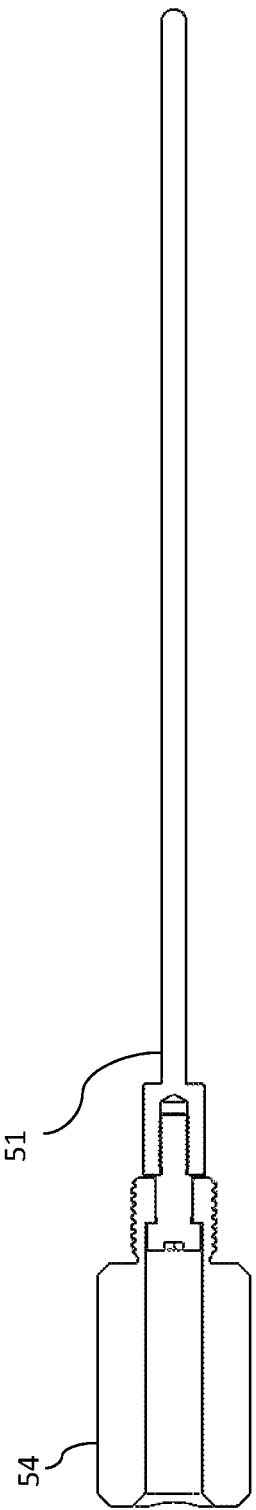
FIG. 45 is a cross-section view of the pushrod used with the second embodiment of the spacer.
Figure 52:
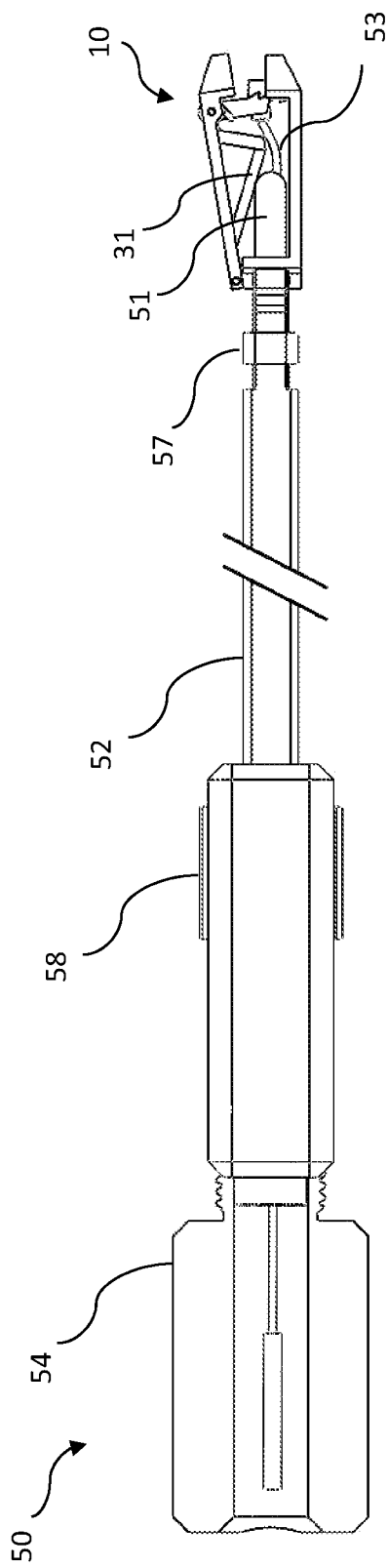
FIG. 52 is a side view of the inserter and spacer showing the unlocking cable attached to the ratchet locking mechanism in the spacer of the second embodiment.

For the second embodiment of the spacer having a single ramp, the pushrod 51 is preferably not articulated at the end, as shown in in FIGS. 43-45. As the pushrod 51 is extended into the cage 13, the pushrod slides along the bottom plate 12 below the top ramp 31, forcing the top and bottom plates apart as it does deeper into the cage. See FIGS. 46-47. Once the top and bottom plates are resting the desired angle, the pushrod 51 is withdrawn. See FIG. 48. Bone graft material 44 is then packed into the spacer.

Figure 53:
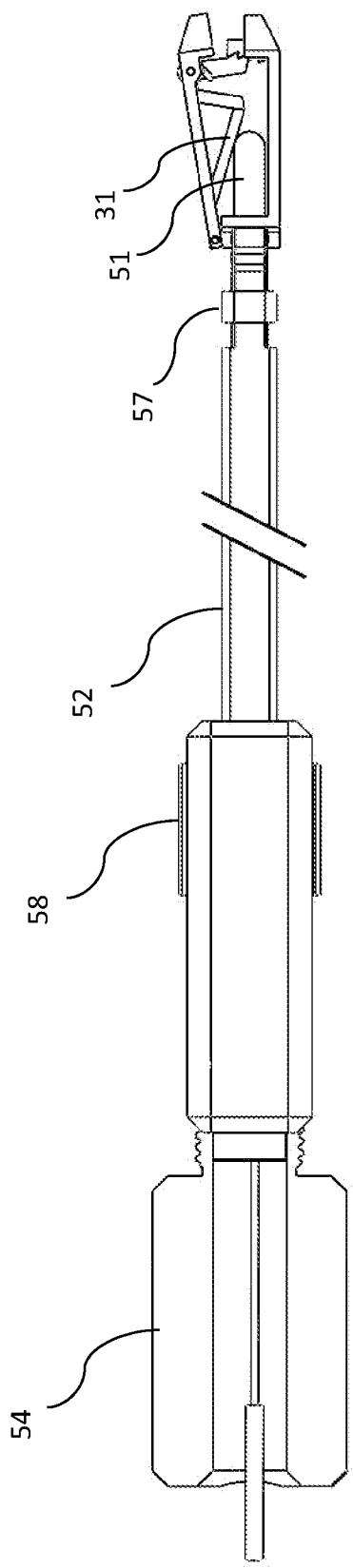
FIG. 53 is FIG. 52 showing the unlocking cable disconnected and withdrawn from the ratchet locking mechanism.

Optionally an unlock cable 53 resides in the cannulated pushrod 51. See FIGS. 49-52. The cable 53 attaches to the movable post 21 with a connection 61. Preferably the connection is threaded but other fastening means may be used. When the cable is pulled proximally, it rotates the movable post 21 away from the stationary post 22, disengaging the saw teeth and permitting the top plate to fall back to a lower position relative to the bottom plate, thereby decreasing the angle between the plates. To disconnect the cable from the post, the cable unfastened and withdrawn from the cage. See FIG. 53.

Once the spacer is in its desired position, the clamp arms are released from the cage by turning the threaded cylinder and the insertion tool is removed from the patient.

Figure 4:
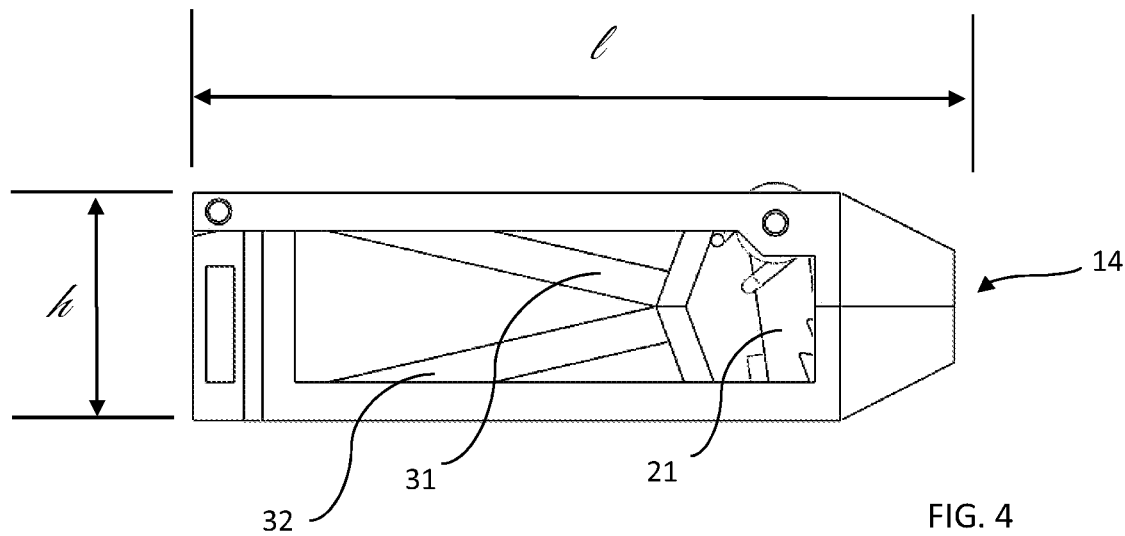
FIG. 4 is a side view of the spacer of FIG. 1, shown without the sheath.
Figure 5:
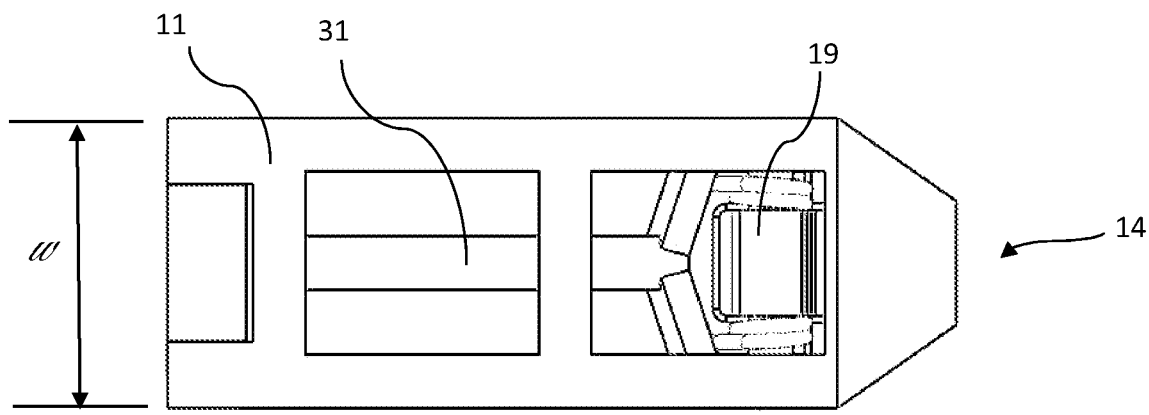
FIG. 5 is a top view of the spacer of FIG. 1.
Figure 6:
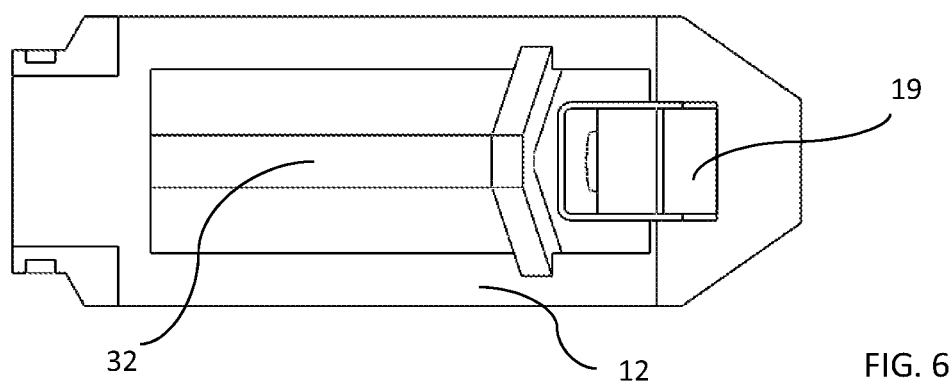
FIG. 6 is a top view of the spacer of FIG. 1 taken along line A-A of FIG. 3.
Figure 7:
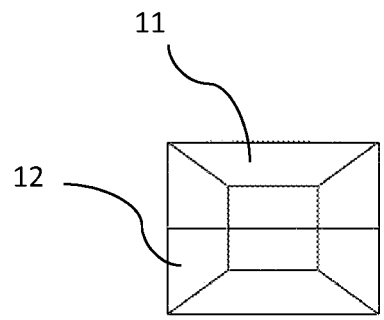
FIG. 7 is an end view of the distal end of the spacer of FIG. 1.
Figure 14:
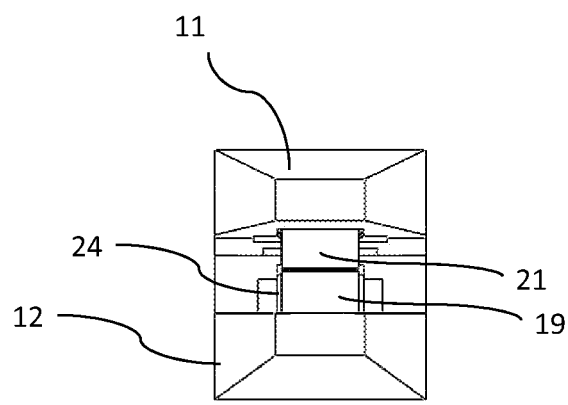
FIG. 14 is an end view of the distal end of the spacer of FIG. 9.
Figure 8:
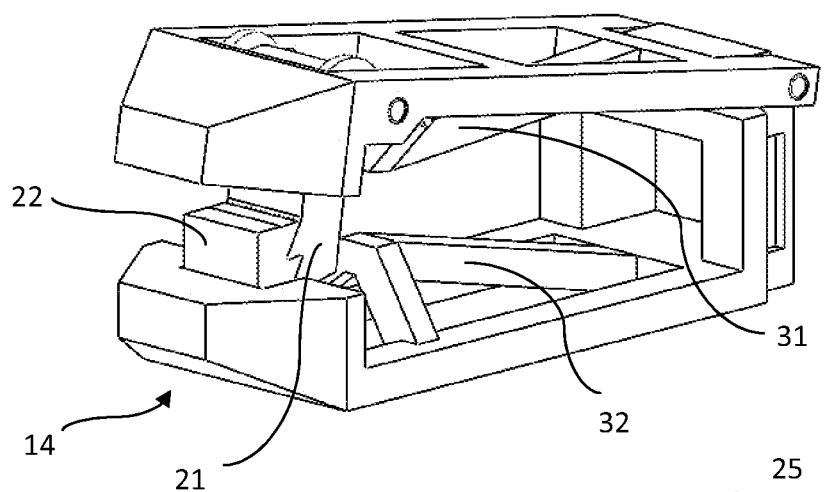
FIG. 8 is a top perspective view from the distal end of the spacer of FIG. 1 in an expanded configuration, shown without the sheath.
Figure 9:
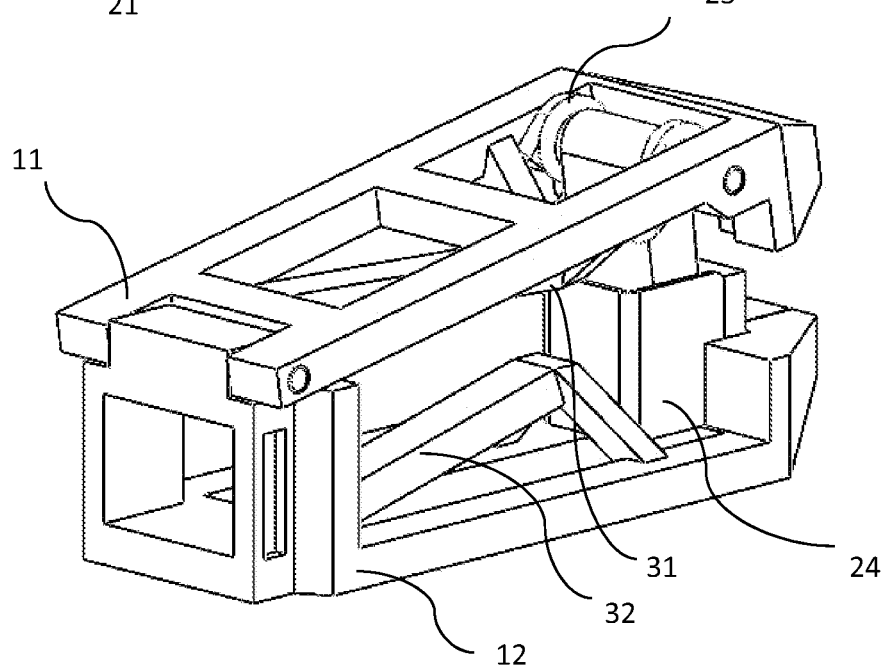
FIG. 9 is a top perspective view from the proximal end of the spacer in FIG. 8.
Figure 10:
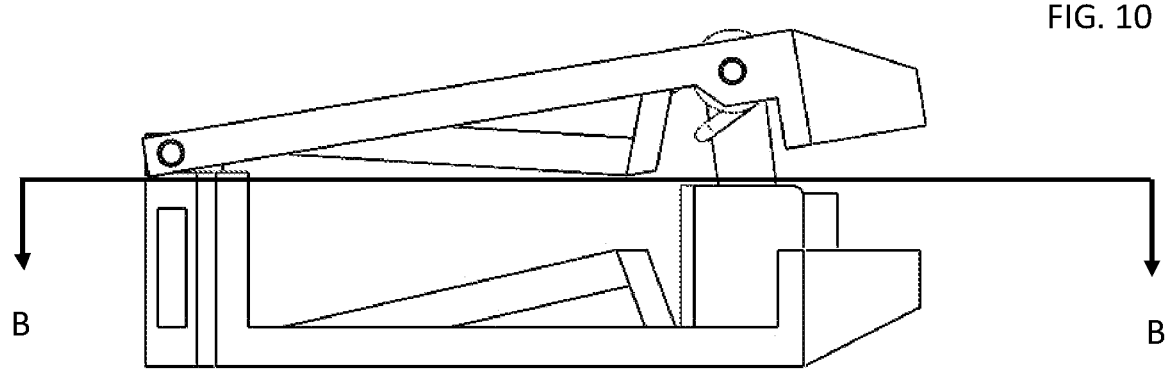
FIG. 10 is a side view of the spacer of FIG. 9.
Figure 11:
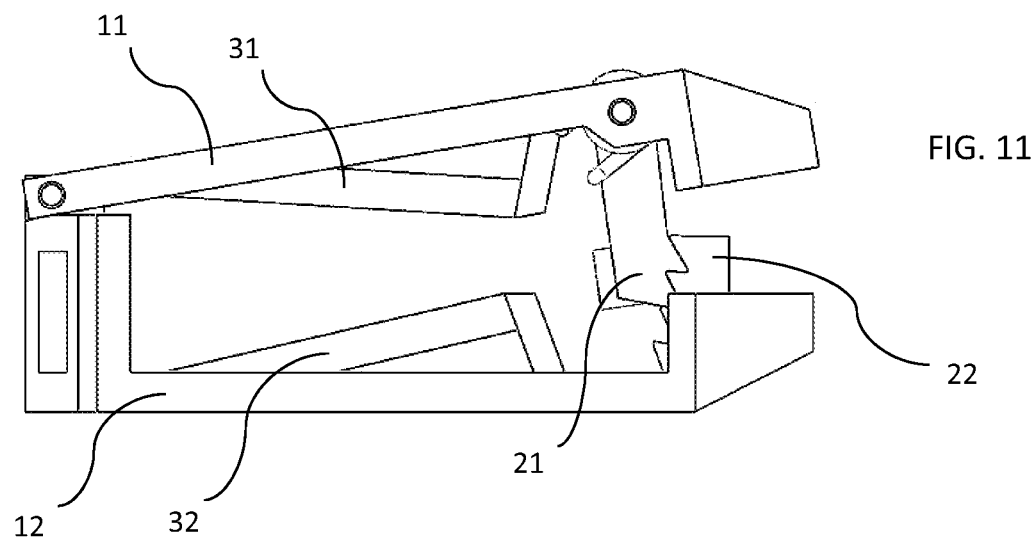
FIG. 11 is a side view of the spacer of FIG. 9, shown without the sheath.
Figure 12:
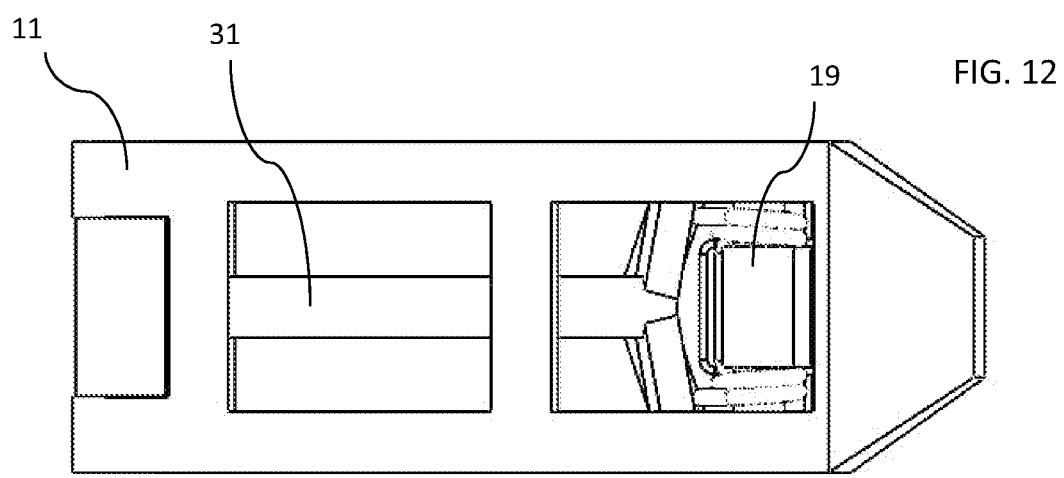
FIG. 12 is a top view of the spacer of FIG. 8.
Figure 13:
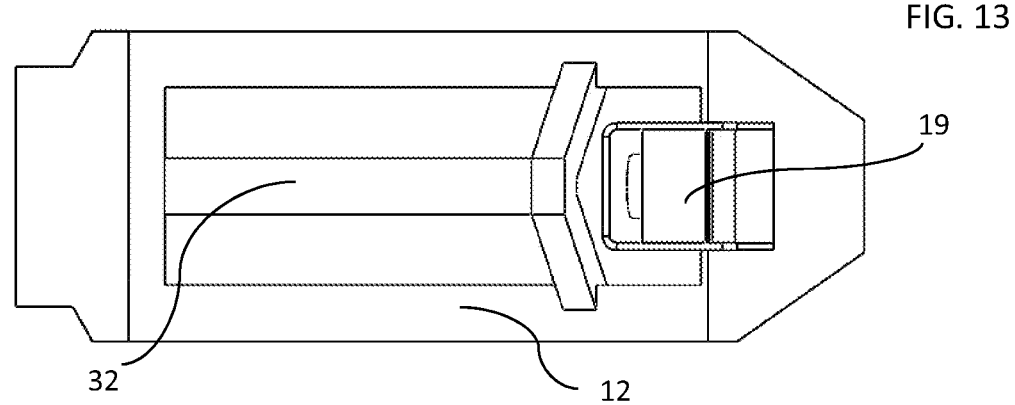
FIG. 13 is a top view of the spacer of FIG. 1 taken along line B-B of FIG. 10.

The spacer is made of a biocompatible material, typically titanium or titanium alloy, and may be made in several sizes. They are typically between 26-30 mm long and 10-11 mm wide. Table 1 shows an exemplary range of sizes, where the height h of the spacer, the width w, and the length l, are shown in FIGS. 4 and 5.

TABLE 1

| Unexpanded Height $h_1$ (mm) | Fully expanded height $h_2$ (mm) at distal end | Angle formed | Width w (mm) | Length l (mm) |
| --- | --- | --- | --- | --- |
| 7 | 10 | 0-16 | 10 | 28 |
| 8 | 12 | 0-16 | 10 | 28 |
| 9 | 14 | 0-16 | 10 | 28 |
| 10 | 16 | 0-16 | 10 | 28 |

Although the general shape of vertebrae 9 are common between patients, the specific size, shape, lordosis, and condition of the cancellous bone are peculiar to each patient. These biological factors affect the size, shape and placement of the spacer. Each plate may be flat, concave or convex, depending on the shape needed to most closely match the curvature of the surfaces of the patient's vertebrae.

Figure 58:
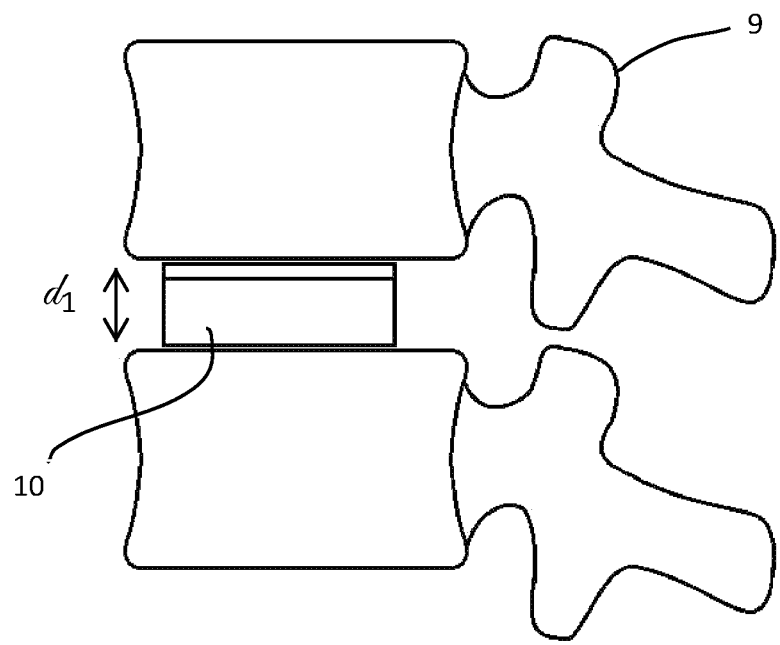
FIG. 58 is a schematic illustration of an unexpanded spacer between two vertebrae.
Figure 59:
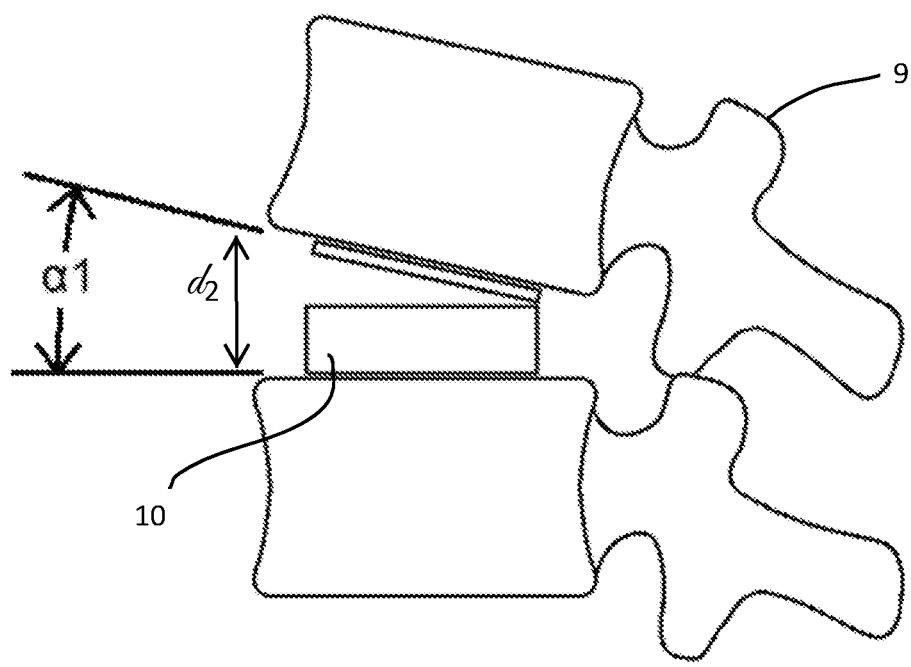
FIG. 59 is a schematic illustration of the spacer of FIG. 58 in an expanded state.

FIG. 58 shows a single unexpanded spacer 10 inserted between two vertebrae 9 which are separated by a distance $d_1$. FIG. 59 shows that single spacer 10 expanded between the two vertebrae 9, forcing the vertebrae 9 apart a distance $d_2$ and angle $\alpha 1$.

While there has been illustrated and described what is at present considered to be the preferred embodiment of the present invention, it will be understood by those skilled in the art that various changes and modifications may be made and equivalents may be substituted for elements thereof without departing from the true scope of the invention. Therefore, it is intended that this invention not be limited to the particular embodiment disclosed, but that the invention will include all embodiments falling within the scope of the appended claims.

What is claimed is:

1. An expandable intervertebral spacer system, the spacer system comprising:

a) a top plate and a bottom plate forming a cage that has a proximal end, a distal end, a top, a bottom, and four sides;
b) a first ramp extending into the cage from the top or bottom of the cage;
c) a hinge connecting the top plate and bottom plate at the proximal end;
d) a stanchion at the distal end, the stanchion comprising a movable post having saw teeth and a stationary post having saw teeth; and
e) a torsion spring configured to bias the movable post against the stationary post, such that the movable post and stationary post cooperate to lock the top plate and bottom plate apart a desired distance.

2. The system according to claim 1 wherein the top, the bottom, and at least three of the four sides of the cage have a cutout.

3. The system according to claim 1 wherein the torsion spring exerts a rotary force on the movable post around a longitudinal axis of the torsion spring.

4. The system according to claim 1 wherein the cage has a longitudinal centerline and the first ramp is disposed at the centerline.

5. The system according to claim 1 further comprising a second ramp extending into the cage from the same plate the first ramp extends from, wherein the cage has a longitudinal centerline and the first and second ramps are disposed on opposite sides of the centerline and at equal distances from the centerline.

6. The system according to claim 1 further comprising a removable insertion tool comprising an extendable pushrod insertable between the top plate and bottom plate from the proximal end which cooperates with the first ramp to force the top plate and bottom plate apart.

7. The system according to claim 6 wherein the insertion tool further comprises an unlock cable removably mated to the movable post.

8. The system according to claim 1 wherein the cage is moveable between a collapsed configuration and an expanded configuration, and wherein in the expanded configuration the top plate and bottom plate are not parallel.

9. An expandable intervertebral spacer system, the spacer system comprising:
a) a top plate and a bottom plate forming a cage that has a proximal end and a distal end;
b) a first ramp extending into the cage from the top plate or bottom plate;
c) a second ramp extending into the cage from the other of the top or bottom plate different from the plate the first ramp extends from, wherein the cage has a longitudinal centerline and the first and second ramps are disposed parallel to the centerline;
d) a hinge connecting the top plate and bottom plate at the proximal end;
e) a stanchion at the distal end, the stanchion comprising a movable post having saw teeth and a stationary post having saw teeth; and
f) a torsion spring configured to bias the movable post against the stationary post, such that the movable post and stationary post cooperate to lock the top plate and bottom plate apart a desired distance.

10. An expandable intervertebral spacer system, the spacer system comprising:
a spacer comprising:
a) a top plate and a bottom plate forming a cage that has a proximal end, a distal end, a top, a bottom, and four sides;
b) a first ramp extending into the cage from the top of the cage and a second ramp extending into the cage from the bottom of the cage;
c) a hinge connecting the top plate and bottom plate at the proximal end;
d) a stanchion at the distal end, the stanchion comprising a movable post having saw teeth and a stationary post having saw teeth; and
e) a torsion spring configured to bias the movable post against the stationary post, such that the movable post and stationary post cooperate to lock the top plate and bottom plate apart a desired distance.

11. The system according to claim 10 wherein the top, the bottom, and at least three of the four sides of the cage have a cutout.

12. The system according to claim 10 wherein the torsion spring exerts a rotary force on the movable post around a longitudinal axis of the torsion spring.

13. The system according to claim 10 further comprising a removable insertion tool comprising an extendable pushrod having a tip, wherein the pushrod is insertable between the top plate and bottom plate from the proximal end which cooperates with the first ramp to force the top plate and bottom plate apart.

14. The system according to claim 13 wherein the insertion tool further comprises an unlock cable removably mated to the movable post.

15. The system according to claim 10 wherein the spacer is moveable between a collapsed configuration and an expanded configuration, and wherein in the expanded configuration the top plate and bottom plate are not parallel.

16. An expandable intervertebral spacer system, the spacer system comprising:
a spacer comprising:
a) a top plate having a top ramp extending toward a bottom plate;
b) the bottom plate having a bottom ramp extending toward the top plate;
the top plate and the bottom plate forming a cage that has a proximal end and a distal end;
c) a hinge connecting the top plate and bottom plate at the proximal end;
d) a stanchion at the distal end, the stanchion comprising a movable post having saw teeth and a stationary post having saw teeth; and
e) a torsion spring configured to bias the movable post against the stationary post, such that the movable post and stationary post cooperate to lock the top plate and bottom plate apart a desired distance;
and
a removable insertion tool comprising an extendable pushrod having a tip, wherein the pushrod is insertable between the top plate and bottom plate from the proximal end which cooperates with the first ramp to force the top plate and bottom plate apart,
wherein the pushrod is articulated at its tip.

17. An expandable intervertebral spacer system, the spacer system comprising:
a) a top plate and a bottom plate forming a cage that has a proximal end, a distal end, a top, a bottom, and four sides;
b) a ramp extending into the cage from either the top plate or bottom plate of the cage;
c) a hinge connecting the top and bottom plates at the proximal end;

d) a stanchion at the distal end, the stanchion comprising a movable post having saw teeth and a stationary post having saw teeth; and e) a torsion spring configured to bias the movable post against the stationary post, such that the movable post and stationary post cooperate to lock the top plate and bottom plate apart a desired distance;

and f) a removable insertion tool comprising an extendable pushrod insertable between the top plate and bottom plate from the proximal end which cooperates with the ramp to force the top plate and bottom plate apart.

18. The system according to claim 17 wherein the top, the bottom, and at least three of the four sides of the cage have a cutout.

19. The system according to claim 17 wherein the insertion tool further comprises an unlock cable removably mated to the movable post.

20. The system according to claim 17 wherein the cage is moveable between a collapsed configuration and an expanded configuration, and wherein in the expanded configuration the top plate and bottom plate are not parallel.

21. An expandable intervertebral spacer system, the spacer system comprising:

a) a top plate and a bottom plate forming a cage that has a proximal end, a distal end, a top, a bottom, and four sides;

b) a ramp extending into the cage from the top or bottom of the cage;

c) a hinge connecting the top plate and bottom plate at the proximal end;

d) a stanchion at the distal end, the stanchion comprising a movable post having saw teeth and a stationary post having saw teeth, wherein:

i) each of the saw teeth has a horizontal edge;

ii) the horizontal edge of the saw teeth on the stationary post are at an angle greater than 90 degrees with respect to the stationary post; and iii) the horizontal edge of the saw teeth on the movable post are at an angle with respect to the movable post that is complementary to the saw teeth on the stationary post; and e) a torsion spring configured to bias the movable post against the stationary post, such that the movable post and stationary post cooperate to lock the top plate and bottom plate apart a desired distance.

\* \* \* \* \*